(12) United States Patent
Gomez Varela

(10) Patent No.: US 11,433,323 B2
(45) Date of Patent: Sep. 6, 2022

(54) PLASMA/SERUM SEPARATOR DEVICE AND METHODS USING THE SAME

(71) Applicant: Max-Planck-Gesellschaft zur Förderung der Wissenschaften e.V., Munich (DE)

(72) Inventor: David Gomez Varela, Goettingen (DE)

(73) Assignee: Max-Planck-Gesellschaft zur Förderung der Wissenschaften e.V, Munich (DE)

( * ) Notice: Subject to any disclaimer, the term of this patent is extended or adjusted under 35 U.S.C. 154(b) by 461 days.

(21) Appl. No.: 16/610,180

(22) PCT Filed: Apr. 30, 2018

(86) PCT No.: PCT/EP2018/061035
§ 371 (c)(1),
(2) Date: Nov. 1, 2019

(87) PCT Pub. No.: WO2018/202622
PCT Pub. Date: Nov. 8, 2018

(65) Prior Publication Data
US 2021/0086106 A1    Mar. 25, 2021

(30) Foreign Application Priority Data

May 2, 2017    (EP) .................................. 17169042
Oct. 10, 2017    (EP) .................................. 17195803

(51) Int. Cl.
*B01D 21/26*    (2006.01)
*B01D 61/14*    (2006.01)
(Continued)

(52) U.S. Cl.
CPC ......... *B01D 21/262* (2013.01); *B01D 61/147* (2013.01); *B01D 69/02* (2013.01);
(Continued)

(58) Field of Classification Search
CPC ............ B01D 21/262; B01D 2325/022; B01D 61/147; B01D 69/02; G01N 33/491;
(Continued)

(56) References Cited

U.S. PATENT DOCUMENTS

| 5,766,962 A | 6/1998 | Childs et al. |
| 5,798,272 A | 8/1998 | Allen et al. |

(Continued)

FOREIGN PATENT DOCUMENTS

| EP | 1843156 A2 | 10/2007 |
| WO | 2009050435 A1 | 4/2009 |

(Continued)

OTHER PUBLICATIONS

European Search Report in corresponding European Patent Application No. 20188456.6, dated Jan. 11, 2021.

(Continued)

*Primary Examiner* — Jennifer Wecker
*Assistant Examiner* — Kathryn Elizabeth Limbaugh
(74) *Attorney, Agent, or Firm* — Westman, Champlin & Koehler, P.A.

(57) ABSTRACT

The present invention relates to a device for separation of plasma or serum from a blood sample from a small blood volume (e.g. capillary blood). The device comprises a separation member, an extraction member and a housing. The extraction member comprises a base and one or more microstructures protruding from and being integrally formed with said base, wherein said one or more microstructures are configured to extract plasma or serum from said separation member by capillary forces. The present invention further provides methods for separating plasma or serum using the device according to the present invention. Similarly, also methods for analyzing one or more proteins and/or metabo- (Continued)

Figure 1A:
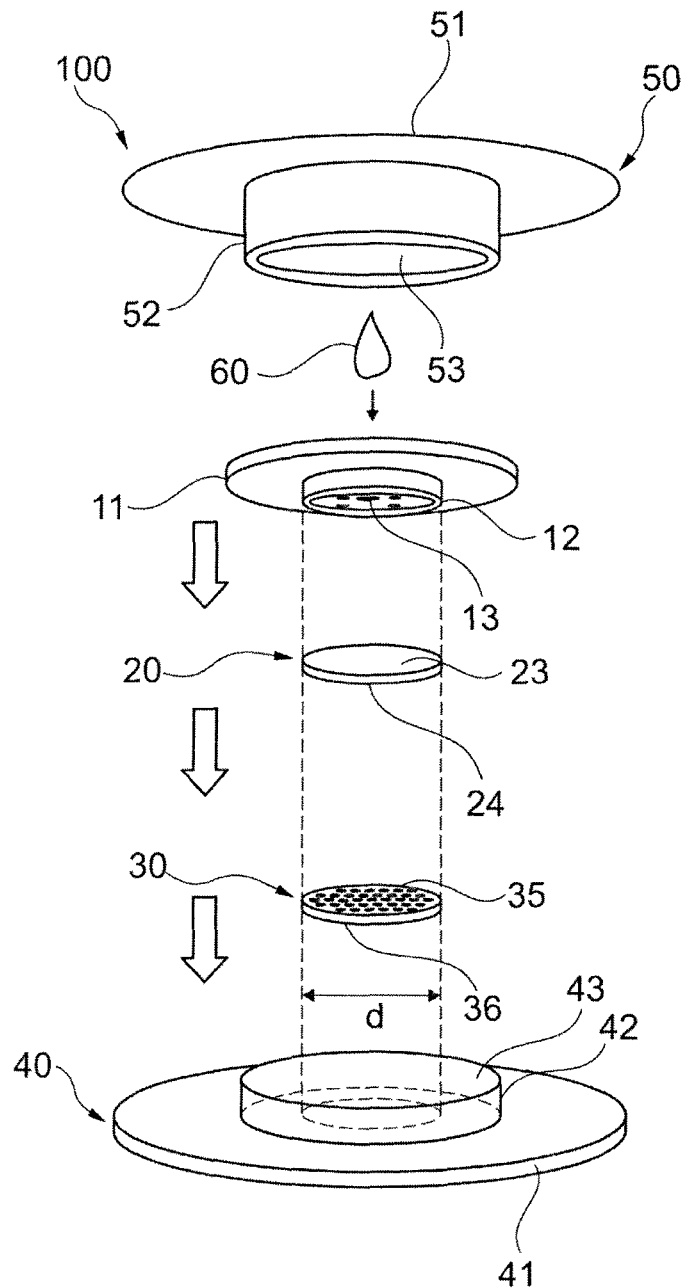
Figure 1B:
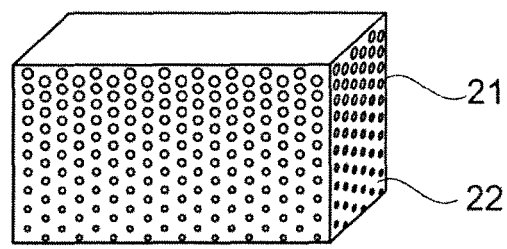

lites contained in plasma or serum that is separated using a device according to the present invention are provided.

20 Claims, 14 Drawing Sheets

(51) Int. Cl.
*B01D 69/02* (2006.01)
*G01N 33/49* (2006.01)
*G01N 33/68* (2006.01)

(52) U.S. Cl.
CPC .......... *G01N 33/491* (2013.01); *G01N 33/68* (2013.01); *B01D 2325/022* (2013.01)

(58) Field of Classification Search
CPC .... G01N 33/68; G01N 33/53; G01N 33/6893; G01N 2800/044; C12Q 2600/156; C12Q 2600/158
See application file for complete search history.

(56) References Cited

U.S. PATENT DOCUMENTS

| | | | |
|---|---|---|---|
| 7,407,742 | B2 | 8/2008 | Ikeda |
| 7,459,125 | B1 | 12/2008 | Stankov et al. |
| 9,222,931 | B2 | 12/2015 | Pfaff et al. |
| 2004/0171173 | A1 | 9/2004 | Eckermann et al. |
| 2007/0134810 | A1 | 6/2007 | Yang et al. |
| 2012/0024788 | A1 | 2/2012 | Kelso et al. |
| 2015/0090674 | A1 | 4/2015 | Lee et al. |
| 2015/0185233 | A1 | 7/2015 | Raiker et al. |

FOREIGN PATENT DOCUMENTS

| | | | | |
|---|---|---|---|---|
| WO | | 2015095853 A1 | 6/2015 | |
| WO | WO-2016025726 A1 | * | 2/2016 | ........... G01N 33/491 |

OTHER PUBLICATIONS

Farrah, Terry et al., "A high-confidence human plasma proteome reference set with estimated concentrations in peptideatlas," Molecular Cellular Proteomics 10.9 (2011) (14 pages).

Panayotov, Ivan Vladislavov et al., "Polyetheretherketone (PEEK) for medical applications," Journal of Materials Science: Materials in Medicine 27:118 (2016) (11 pages).

International Search Report and Written Opinion of the International Search Authority dated Jul. 19, 2018, for corresponding International Application PCT/EP2018/061035, filed Apr. 30, 2018.

Extended European Search Report dated May 8, 2018, in corresponding European application No. 17195803.6.

Carr, S.A. et al. Targeted peptide measurements in biology and medicine: best practices for mass spectrometry-based assay development using a fit-for-purpose approach. Molecular & Cellular Proteomics:MCP 13, p. 907-917, 2014.

Drucker, E. & Kraphenbauer K., Pitfalls and limitations in translation from biomarker discovery to clinical utility in predictive and personalised medicine, The EPMA journal 4, 7, 2013.

Huttenhain, R. et al. Reproducible quantification of cancer-associated proteins in body fluids using targeted proteomics. Science translational medicine 4, 142ra194 2012 (author manuscript version, 25 pages).

Proc, J et al. A quantitative study of the effects of chaotropic agents, surfactants, and solvents on the digestion efficiency of human plasma proteins by trypsin. J Proteome Res.9(10): p. 5422-5437, 2010 (author manuscript version, 30 pages).

Rouwette, T. et al. Standardized Profiling of The Membrane-Enriched Proteome of Mouse Dorsal Root Ganglia (DRG) Provides Novel Insights Into Chronic Pain. Molecular & Cellular Proteomics:MCP 15, p. 2152-2168, 2016.

Shi, T. et al. Advances in targeted proteomics and applications to biomedical research Proteomics 16, p. 2160-2182, 2016 (author manuscript version, 37 pages).

WHO Guidelines on Drawing Blood: Best Practices in Phlebotomy; Geneva; 2010 (125 pages).

"The Deluxe Deep Dive". WellnessFX; https://web.archive.Org/web/20161220044239/http://www.wellnessfx.com/premium (archived Dec. 20, 2016) (2 pages).

"Choosing the Right Package". WellnessFX; https://web.archive.org/web/20161214115104/http7/www.wellnessfx.com/packages (archived Dec. 14, 2016) (3 pages).

"Getting Started With WellnessFX". WellnessFX; https://web.archive.org/web/20161213172408/http://www.wellnessfx.com/how-it-works (archived Dec. 13, 2016) (2 pages).

"Not Your Average Blood Test". WellnessFX; https://web.archive.org/web/20161220061121/http://www.wellnessfx.com/ (archived Dec. 20, 2016) (3 pages).

* cited by examiner

PLASMA/SERUM SEPARATOR DEVICE AND METHODS USING THE SAME

The present application is a § 371 national phase entry of International patent application Serial No. PCT/EP2018/061035, files Apr. 30, 2018, and published in English, and claims priority from EP application no. 17 16 9042.3 filed on May 2, 2017 and EP application no. 17 19 5803.6 filed on Oct. 10, 2017, each of which is incorporated herein by reference in its entirety.

The present invention relates to a plasma/serum separator device and methods employing such device.

Blood is a window to our health. As such, it is the most used biofluid in discovery of biomarkers and in routine health checks. In both of these fields several handling processes are necessary during the blood sampling protocol in order to obtain the value of the analytes of interest. Unfortunately, these handling steps are not standardized among different blood sampling facilities and include several manual operations that introduce variability in the process and therefore hamper the quality of the analytical results. Furthermore, many of these blood-sampling processes require trained technicians or expensive instrumentation making them unsuitable for resource limited locations or point-of-care (POC) testing. Separation of serum or plasma from a whole blood sample is one of the particularly critical steps during handling of blood samples that is especially prone to introducing variability in the measurement of certain analytes such as e.g. biomarker proteins or metabolites. Moreover, separation of serum or plasma currently requires trained personal and expensive instruments such as centrifuges. The separation of serum and plasma is therefore not yet available in a ready-to-costumer setting.

Accordingly, there is a high need to provide means and methods for improving separation of plasma or serum from whole blood samples. Specifically, there is a need to provide means and methods for serum/plasma separation that improve the reproducibility in analyte detection, i.e. which minimize the influence of the serum/plasma separation on the amount of the analyte detected. Further, there is a high need to provide means and methods for separation of plasma or serum from whole blood samples that are easier to handle and that can ideally even be handled without the need for intervention by trained personnel or the requirement of special instruments.

Analysis of plasma or serum samples is of particular importance in the field of biomarker discovery and analysis. Since the emergence of the so-called "omics" techniques thousands of putative biomarkers detected in serum or plasma samples have been identified and published. However, there is a growing gap between the published biomarkers and the amount of them that get finally approved (Drucker, E. & Krapfenbauer, K., *Pitfalls and limitations in translation from biomarker discovery to clinical utility in predictive and personalised medicine*, The EPMA journal 4, 7, 2013). This difference is due to major limitations in both the methodology and the technologies used for biomarker discovery. The discovery and/or analysis of biomarkers (e.g. disease biomarkers) derived from blood is normally initiated by several steps aiming to separate the plasma/serum liquid phase (containing the biomarker of interest; e.g. proteins) from the solid phase (containing cellular components; e.g. red blood cells) of the blood; i.e. the separation of serum or plasma from blood samples. In a biomedical laboratory setting, this process is typically carried out by centrifugation of the blood specimen, followed by manually pipetting out the liquid plasma/serum phase. However, the lack of a universal protocol together with the required manual steps (e.g. pipetting) introduces considerable amount of variability that finally has a negative impact on the reproducibility of the analytical process. Specific variables that may have an impact on the biomarker profiling results are, for example, the selected anticoagulant, the centrifugation time and speed and the storage conditions. These variables become particularly critical when it comes to the analysis of easy-to-degrade molecules such as proteins or metabolites, which are abundantly measured in biomarker discovery and routine analysis. Thus, there is a need to provide means and methods that reduce the pre-analytical variability during the preparation of serum/plasma from blood samples for subsequent biochemical analysis of said samples, e.g. for biomarker discovery and/or analysis. In particular, there is a need to provide means and methods for separating plasma or serum from blood that minimize the influence of the separation process on downstream measurement, e.g. of unstable analytes such as proteins or metabolites in plasma/serum samples. Further, as it may be highly desirable to store serum/plasma before analysis, there is also a need for means and methods for separation of plasma or serum from whole blood that allow for improved plasma/serum storage after separation.

Blood samples and in particular separation of serum/plasma from said blood samples is also of high importance in the growing field of personalized medicine. Medicine in the XXI century is moving from a "one-size-fits-all" approach to acknowledge the molecular differences between each individual that influence the way a disease develops and therefore the way it can be treated. Currently, personalized medicine is mainly based on technologies analyzing the individual genetic makeup of an individual, i.e. genetic tests. Hundreds of companies currently offer direct-to-costumer genetic tests that deliver specific health status reports through the analysis of genetic variants associated to specific diseases. These types of services normally start with the costumer taking a saliva sample and sending it to the company for analysis. The stability of DNA (that can be easily stored at room temperature for several days) allows customers to take the sample at their home. However, genetic analyses are limited since it is well known that genetic variants do often not reflect the real presence of a disease but only a probability of developing it in the future. Instead, proteins, which are encoded by the genetic information, are the molecules performing the functions in the cells. In many pathological processes, only proteins, but not the genetic information encoding them, are changed (e.g. a change in level or a change in posttranslational modification). Therefore, it is highly desirable to offer future personalized medicine approaches that analyze specific disease-linked proteins (e.g. biomarkers) instead of the genetic information. Since plasma or serum samples are one of the most important sources to study disease-linked proteins, there is a need to provide methods and means for separating plasma or serum from blood samples in which proteins are recovered and preserved reliably and reproducibly for subsequent analysis. In particular, there is a need to provide means and methods for the separation of plasma or serum from whole blood that do only involve a minimum or no intervention of trained personnel (comparable to genetic tests based on saliva samples) and/or a minimum of specialized equipment, but still preserve proteins. Another problem in the field of protein-based personalized medicine is that until now most available tests are limited to single proteins or a small subset of proteins. This is due to the use of antibody-based analyses (immunoassays) for detecting changes in the status of few specific proteins in blood. Such antibody-based analyses have the following disadvantages: i) they are limited in the amount of proteins that can be analyzed in parallel and, thus, limited in scope when trying to track the whole health status of a person (blood comprises thousands of proteins), and ii) they increase the variability of the results, because they rely on the performance of antibodies that, although they act against the same protein target, have distinct characteristics (e.g. are produced in different species or bind to different epitopes of the target protein) and may therefore introduce a random error. In addition to these technical limitations, pioneer personalized protein analysis services (e.g. offered by WellnessFX, see https://www.wellnessfx.com) typically use venous blood and therefore require the costumer to use specialized blood-drawing services involving trained personnel, making it operationally limited to offer a direct-to-costumer home service. These limitations of antibody-based tests may be addressed by using other methods such as mass spectrometry based analytic methods. To bring this to practice, there is a need to improve methods and means to separate plasma or serum to be more compatible with the requirements of these other methods, such as mass-spectrometry based analysis methods.

Accordingly, in view of the above, there is a clear need for blood-sampling devices that i) will allow the sampling of blood in an easy way (ideally without the need of trained personnel or special instrumentation), ii) will separate the plasma/serum phase without manual intervention or external energy sources and/or iii) will preserve the status of rather unstable molecules in a blood sample such as blood proteins (e.g. biomarker proteins) and/or metabolites in a way that allows their down-stream analysis in a reproducible manner without the need of antibodies, e.g. by using mass spectrometry based analysis methods.

Devices for separating plasma or serum from blood samples have been described in US 2015/0185233 A1, US 2015/0090674 A1 and U.S. Pat. No. 9,222,931 B2. However, separation of plasma or serum using said devices involves an external energy source (e.g. pressure) to remove the plasma or serum from the respective separation member used. This is disadvantageous since it may lead to variability in the amount and/or quality of the recovered plasma/serum. Specifically, there is a high risk that blood cells are lysed (e.g. referred to as hemolysis when red blood cells are lysed) due to the applied external forces when handling these devices. Lysis of cells causes a leakage of otherwise intracellular biomolecules (e.g. proteins, DNA and RNA) to the plasma/serum and the extent of lysis is expected to be very variable. Therefore, the described devices are expected to have a high variability in the biomolecule content of the separated serum/plasma sample, in particular in the content of proteins. This is can negatively affect the reproducibility of downstream analyses, e.g. the determination of protein levels (in particular if a protein is present in the serum and inside the blood cells). Accordingly, there is a need for means and methods for blood plasma or serum separation that do not apply external energy, such as pressure, or only apply reproducible and minimal external energy. Moreover, there is a need to provide means and methods for separating plasma or serum from blood that reduces hemolysis.

WO 2015/095853 A1 describes a device for separating plasma or serum from whole blood comprising a filter module comprising a membrane. However, serum and plasma is not extracted but rather dried on the filter module membrane. Such setup has disadvantages with respect to the capacity of serum or plasma that can be separated, makes an extraction step of plasma or serum necessary that will introduce unknown variability to the whole analytical process, and may negatively affect the stability of unstable analytes, such as proteins.

U.S. Pat. No. 7,407,742 B2 describes a plasma or serum separator, wherein the plasma or serum is separated such that it is located in the distal end portion of a blood separation member of said plasma or serum separator. From said distal end portion the serum is sampled through a sampling aperture by applying external forces such as pressure. Applying external forces for removing the serum/plasma from the separation member has the disadvantages mentioned above.

Furthermore, US 2012/0024788 A1 describes devices and corresponding methods for separating blood plasma from whole blood. The devices described therein comprise a collection element that draws plasma from a filter module. In particular, the collection element comprises a water-insoluble fiber- or paper-based membrane. Collecting plasma with such a fiber- and/or paper-based membrane, however, is believed to have the following drawbacks:

First, the water insoluble fiber- and/or paper-based membrane may have a high absorbing affinity for certain analytes (e.g. certain proteins, metabolites or drugs) which may negatively influence downstream analysis of said analytes.

Second, the collection elements comprising water insoluble fiber- and/or paper-based membranes have only a limited capacity for plasma or serum.

Third, an extraction step (e.g. a chemical extraction step) is required to extract the plasma and/or analytes from the water insoluble fiber- or paper-based membrane to a liquid phase (e.g. saline buffer) for downstream analysis. Such an extraction step may negatively affect analyte stability and/or may lead to loss of analytes that may have more affinity for the fiber or paper-based membrane than for the liquid phase. Furthermore, the analyte extraction adds another step into the analysis procedure that may negatively affect reproducibility of analyte analysis. In particular, due to different affinities of different analytes to the water insoluble fiber-based or paper-based membrane, not every analyte may be recovered by an extraction step to the same extent.

The object of the present invention is to address one or more of the above-mentioned needs and/or to overcome one or more of the above-mentioned limitations of previously described plasma/serum separation devices and/or methods.

According to a first aspect, the present invention provides a device for separation of plasma or serum from a blood sample, said device comprising a separation member configured to separate plasma or serum from cellular blood components and an extraction member. The device may further comprise a housing. In some instances, the separation member could be omitted. For example, the device could be sold without the separation member, which could then be inserted by the user itself.

The separation member of the device preferably has a separation member upper surface and an opposing separation membrane lower surface, wherein said upper surface or at least a portion thereof is preferably configured to receive a blood sample. Preferably, said separation member is configured to separate plasma or serum from cellular blood components by retaining cellular blood components (preferably in the upper part of the separation member). In other words, the separation member may be configured to retain cellular blood components in a first portion of the separation member (preferably in the upper portion of the separation member) and to allow only plasma or serum to pass through the separation member, preferably so that it accumulates in and/or can be extracted from a second portion of the separation member (preferably the lower portion of the separation member).

The extraction member of the device is preferably configured to extract plasma or serum from the separation member, preferably the portion of the separation member where the plasma or serum accumulates during separation, i.e. preferably the lower part of the separation member. Preferably, the extraction member comprises or consists of a base and one or more microstructures protruding from said base, wherein the upper surface of said one or more microstructures form an extraction member upper surface. The extraction member and/or the one or more microstructures thereof are preferably configured to extract plasma or serum from the separation member (preferably the lower part thereof) by capillary forces. In other words, the extraction member and/or the microstructures (in particular also the upper surface of said microstructures) may be configured to generate capillary forces in order to extract plasma and or serum from the separation member (preferably the separation member lower portion). Preferably, the base of the extraction member and the one or more microstructures protruding from said base are integrally formed. The one or more microstructures may preferably protrude (substantially) orthogonally from the base. Similarly, the one or more microstructures may protrude (substantially) perpendicularly from said base. Potentially, the extraction member used in any of the devices described herein could also be a water soluble cellulose, in particular a carboxymethyl cellulose (AquaCell® Extra™). The water soluble cellulose preferably is configured to completely dissolve in a liquid phase like distilled water and/or a saline buffer (e.g. PBS or Phosphate buffer saline), preferably within 60 min. or less, 40 min. or less, more preferably 30 min. or less, therefore freeing all proteins and/or metabolites in the liquid phase.

Accordingly, the device for separation of plasma or serum from a blood sample according to the present invention may preferably comprises:

a housing, a separation member configured to separate plasma or serum from cellular blood components by retaining said cellular components of blood, wherein said separation member has a separation member upper surface and an opposing separation member lower surface, and wherein said separation member upper surface or a portion thereof is configured to receive a blood sample, and an extraction member for extracting the separated plasma or serum from the separation membrane, wherein said extraction member comprises or is composed of a base and one or more microstructures protruding from and being integrally formed with said base, wherein the upper surface of said one or more microstructures forms an extraction member upper surface, and wherein said one or more microstructures are configured to extract plasma or serum from said separation member by capillary forces.

The extraction member of a device of the present invention is preferably disposed below the separation member. This configuration is particularly preferred when the separation member is configured in a manner that the separated serum/plasma passes to the lower separation member portion.

Accordingly, the extraction member upper surface may be in contact with the separation member lower surface, preferably in intimate contact with the separation member lower surface. Having a contact or intimate contact between the separation member lower surface and the extraction member upper surface allows for capillary forces that originate from a structure of the extraction member to promote extraction of the serum or plasma from the separation member, where it is separated from the cellular blood components. It is, for example, envisaged that at least 50%, at least 60%, at least 80%, or at least 90% or even 100% of said extraction member upper surface may be in contact (preferably intimate contact) with the separation member lower surface. In principle, a close contact (preferably intimate contact) between the separation member lower surface and the extraction member upper surface is preferred, because close contact (preferably intimate contact) may increase the efficiency of extracting/drawing serum/plasma from the separation device.

Accordingly, in other words, the amount of serum extracted from the separation member may be increased thereby.

The extraction member of the device of the present invention may further be configured to collect and/or store plasma or serum extracted from the separation member. In other words the extraction member may comprise cavities for collecting and/or storing the plasma or serum extracted from the separation member. Said cavities are preferably formed between the microstructures protruding from the base of the extraction member when the extraction member comprises such microstructures. In other words, the separated serum or plasma may be collected or stored in the space between the one or more microstructures protruding from the base of the extraction member. When configured to collect and/or store separated plasma or serum such extraction member may also be referred to as a collection member.

It is preferred in the context of the present invention that the extraction member of the device comprises or is composed of a base and one or more microstructures protruding from said base. Said base and said one or more microstructures may be integrally formed. Further, the upper surfaces of said one or more microstructures may form an extraction member upper surface, wherein said one or more microstructures are configured to extract plasma or serum from said separation member by capillary forces. A skilled person will appreciate that such a configuration may, for example, include a surface having gaps, or holes whereby capillary forces can be generated.

The one or more microstructures may have a height of (about) 0.1 mm to (about) 1 mm, preferably of (about) 0.2 mm to (about) 0.7 mm, even more preferably (about) 0.3 mm to (about) 0.5 mm and most preferably of (about) 0.3 mm. As illustrated in the appended Examples and Figures, microstructure height influences the amount of plasma or serum that can be recovered in the extraction member. With the dimensions indicated the amount of plasma/serum extracted from the separation member can be increased, i.e. the yield of separated plasma/serum is increased.

The one or more microstructures of the extraction member are preferably a plurality of microstructures and the upper surfaces of the plurality of microstructures preferably form the extraction member upper surface. The plurality of microstructures preferably has or substantially has the same height in order to form a plane or substantially plane extraction member upper surface. This is particularly preferred if the lower surface of the separation member is also plane or substantially plane. Alternatively, the height of the microstructures forming the upper surface of the extraction member may also be different so as to form a substantially fitting counterpart to the lower surface of the separation member.

According to the present invention, it is particularly preferred that the plurality of microstructures comprises micro-pillars. Most preferably, the plurality of microstructures is a plurality of micro-pillars (or an array of micro-pillars). The advantage of the plurality of microstructures being micro-pillars is that they can be easily and flexibly formed on the base of the extraction member. In particular, such microstructures can be positioned relatively to each other such that the desired capillary forces are provided and/or a desired empty volume/cavities between the micro-pillars for collecting and/or storing separated plasma/serum is defined. Accordingly, a setup using micro-pillars as the one or more microstructures allows flexibly adapting the volume that can be held, collected or stored in the extraction member. In particular, the extraction member may be configured to hold volumes larger than known paper- or fiber-based extraction members of the same size can hold (due to their saturation limit).

A micro-pillar may in principle have different cross sections. In the plurality of micro-pillars, all or essentially all of the micro-pillars may have the same or substantially the same cross-section. Alternatively, also micro-pillars with different cross-sections may be combined in the plurality of micro-pillars. Similarly, the dimensions of the cross-sections may be the same or substantially the same. However, in principle also micro-pillars having different dimensions of the cross-sections may be comprised in the plurality of micro-pillars.

For instance, one or more, or all of the micro-pillars may have a (substantially) rectangular cross section. A rectangular cross section may have a length of (about) 0.2 mm to (about) 3 mm, preferably (about) 0.5 mm to (about) 2 mm, more preferably (about) 0.8 mm to (about) 1.2 mm and most preferably (about) 1 mm. Further, such micro-pillars with a rectangular cross section may have a width of (about) 0.1 mm to (about) 1.5 mm, preferably (about) 0.2 mm to (about) 1 mm, more preferably (about) 0.3 mm to (about) 0.8 mm and most preferably (about) 0.5 mm.

Moreover, one or more, or all of the micro-pillars may have a (substantially) triangular, quadrilateral, or square cross section. The side length of such cross sections may be between (about) 0.2 mm and (about) 3 mm, preferably between (about) 0.5 mm and (about) 2 mm, more preferably between (about) 0.8 mm and (about) 1.2 mm, and most preferably (about) 1 mm.

Furthermore, one or more, preferably all of the micro-pillars, may have a (substantially) circular cross section. The diameter of a circular cross section may be between (about) 0.2 mm and (about) 3 mm, preferably between (about) 0.5 mm and (about) 2 mm, more preferably between (about) 0.8 mm and (about) 1.2 mm, and most preferably (about) 1 mm.

The extraction member of a device according to the present invention may be provided with one or more channels (which may also be referred to as cavities or pores), preferably a plurality of channels. These one or more channels are preferably formed by the base in conjunction with microstructures that are adjacent to each other. In particular, microstructures may have a certain distance to each other and by said distance a channel may be formed between these microstructures. In other words, the channels may have a bottom that can be formed by the base and sidewalls that can be formed by two adjacent microstructures. The one or more channels are preferably channels in which the separated plasma/serum extracted from the separation device is collected.

The one or more channels may have a height of (about) 0.1 mm to (about) 1 mm, preferably of (about) 0.2 mm to (about) 0.7 mm, even more preferably of (about) 0.3 mm to (about) 0.5 mm and most preferably of (about) 0.3 mm. The height is preferably defined between the upper edge of the channel (or alternatively the maximum height of the protrusions forming the sidewalls) and the channels bottom (e.g. the base of the extraction member). As illustrated in the appended Examples and Figures, the height of the channels influences the amount of plasma or serum that can be recovered in the extraction member. Correlating with indicated preferences the amount of plasma/serum extracted from the separation member can be increased, i.e. the yield of separated plasma/serum can be increased. Without being bound to theory, it is believed that the influence of the channel height on the recovered amount of plasma/serum in the extraction member is achieved by its influence on the capillary forces generated by said extraction member and/or on channel volume One or more or each of the one or more channels of the extraction member may have an opening width at the extraction member upper surface in a top view of said extraction member. The opening width at a specific location of a channel may be defined as the shortest linear distance between the adjacent sidewalls forming the respective channel at this specific location. For example, if the one or more channels have an opening at the extraction member upper surface that in a top view of said extraction member is substantially circular, the opening width may be defined as the diameter of said circular shape. If the opening width has other shapes (e.g. a substantially rectangular shape), the shortest side of the respective shape may be defined to be the opening width. The channels of the extraction member may all have substantially the same opening widths. Alternatively, the one or more channels may also have different opening widths. The median opening width of said one or more channels at the extraction member upper surface (in a top view of said extraction member) may be between (about) 0.1 mm and (about) 2 mm, preferably between (about) 0.3 mm and (about) 1.2 mm, more preferably between (about) 0.4 mm and (about) 0.6 mm, and most preferably (about) 0.5 mm. In a top view of the extraction member, the one or more channels may define a total channel length (which may be defined as the combined length of all channels) and/or a total channel area/surface (which may be defined as the total space between the microstructure(s) at the upper surface of the extraction member. The opening width of said one or more channels at the extraction member upper surface may be at least (about) 1 mm, preferably at least (about) 0.7 mm, and more preferably at least (about) 0.5 mm along at least 50%, at least 60%, at least 70%, at least 80%, or at least 90% of said total channel length and/or said total channel area/surface. Further, at least 50%, preferably at least 60%, more preferably at least 70%, even more preferably at least 80%, and even more preferably at least 90% of the opening width of the one or more channels at the extraction member upper surface (in a top view of said extraction member) may be between (about) 0.1 mm and (about) 2 mm, preferably between (about) 0.3 mm and (about) 1.2 mm, more preferably between (about) 0.4 mm and (about) 0.6 mm, and most preferably (about) 0.5 mm. The opening width of the one or more channels is believed to have an influence on the capillary force generated and may therefore influence the amount of serum/plasma extracted from the separation member. With the above-mentioned dimensions of the opening width of the one or more channel the efficiency of serum or plasma extraction from the separation member is increased, as illustrated in the Examples and Figures below (see, e.g., FIG. 2B).

The one or more microstructures of the extraction member may be positioned at a distance to each other. The median distance between adjacent microstructures may be between (about) 0.1 mm and (about) 2 mm, preferably between (about) 0.3 mm and (about) 1.2 mm, more preferably between (about) 0.4 mm and (about) 0.6 mm, and most preferably (about) 0.5 mm. Similarly, at least 50%, preferably at least 60%, more preferably at least 70%, even more preferably at least 80%, or most preferably at least 90% of adjacent microstructures are arranged with a distance there between of 1.5 mm to 0.2 mm, preferably 1 mm to 0.35 mm, and more preferably 0.75 mm to 0.5 mm. The distance between adjacent microstructures as defined herein is expected to influence the capillary force generated and may therefore influence the amount of serum/plasma extracted from the separation member.

The extraction member of the device according to the present invention may also have an extraction member lower surface. Said extraction member lower surface may be at least one of: continuous, non-porous, non-perforated and/or impermeable to plasma or serum. This has the advantage that serum or plasma cannot only be extracted from the separation member by capillary forces but may also be stored in the extraction member without leakage at the extraction member lower surface. As will be apparent from the discussion below, this allows for an improved handling and performance of the device after performing serum/plasma separation.

As mentioned above, the extraction member of the device according to the present invention preferably comprises a base. Said base may be a base plate. Preferably, the base plate may be rigid, self-supporting and/or unitary. The base or base plate may in particular not be formed from a paper, paper-like or any other fibrous material, in particular not a water absorbing fibrous material. Similarly, also the one or more microstructures (e.g. micro-pillars) may be solid, rigid and/or self-supporting. Preferably, the one or more microstructures (e.g. micro-pillars) may be rigid, self-supporting and/or unitary. The one or more microstructures may in particular not be formed from a paper, paper-like or any other water absorbing fibrous material. It is preferred that the one or more microstructures are formed from the same material as the base. Even more preferably, the one or more microstructures are integrally formed with the base. Accordingly, it is preferred that the extraction member is solid, rigid and/or self-supporting. Similarly, it is preferred that the extraction member is not a membrane or filter, in particular not a paper- or fiber-based membrane or filter. Such extraction members may have the advantage that the serum/plasma extracted from the separation member can be easily stored, e.g. even in a liquid form. In particular, no extraction step is required to remove serum or plasma in a liquid form. In the case of paper- or fiber-based extraction members this may be necessary. The independency of extraction steps may, in particular, also positively contribute to reproducibility of downstream analysis of analytes such as proteins, metabolites or drugs, which may be difficult to reproducibly be extracted from paper- or fiber-based members after being adsorbed thereby. Further, a "self-supporting" extraction member will not deform or not substantially deform under the influence of gravity when being held at one end corner. This facilitates, for example, automatic handling operations of such extraction device (e.g. using robotic sample handling systems).

The base plate of an extraction member may have a thickness of between (about) 0.2 mm and (about) 2 mm, preferably between (about) 0.5 mm and (about) 1.5 mm, and even more preferably between (about) 0.8 mm and (about) 1.2 mm.

The extraction member of the device according to the present invention may be made or formed from plastic, photoresist resin or any polymeric material. For instance, the extraction member may be made (or formed) from a polyamide, preferably a hydrophilic polyamide. The extraction member may, for example, be made (or formed) from nylon, polyether ether keton, acrylic or acrylic-derivatives such as poly(methyl methacrylate), Cyclic Olefin Copolymer, or epoxy SU-8. A particularly preferred material is a polyamide (such as a hydrophilic polyamide) or polyether ether keton since these materials are already used in several clinical settings. The above-mentioned materials have the advantage of being non-water absorbing such as for instance paper-based material. Furthermore, these materials may have hydrophilic properties that can increase the capillary forces generated by the extraction member to extract serum or plasma from the separation member. Accordingly, a device according to the present invention with an extraction member being made of one of said materials has the advantage that the separated serum extracted from the separation membrane can be stored as a liquid and/or may contribute to increase the efficiency of extracting serum/plasma from the separation member. Extraction and/or storage of serum/plasma as a liquid have the advantage that no extraction step using additional liquid or chemicals to gain plasma or serum in a liquid phase is required. Moreover, the above-mentioned materials are believed to have a very low binding affinity to proteins. The appended Examples and Figures exemplary demonstrate this property for polyamide since they demonstrate that analyzing plasma separated from capillary blood using a device according to the present invention that comprises an extraction member being made of polyamide by mass-spectrometry gives comparable results to analysis of venous plasma stored in widely-used Eppendorf tubes. Accordingly, an extraction member made of any one of the above-mentioned materials (and in particular polyamide) is believed to be ideally suitable for separating serum/plasma for downstream analysis of an analyte being a protein, e.g. a biomarker protein. A further advantage of an extraction member being made of any of the materials mentioned above is that it is easy and economical to produce, e.g. with mass production techniques. Injection molding is currently the preferred manufacturing technique, but also other techniques may be feasible, such as hot embossing, computer numerical control (CNC) machining or 3D printing.

The extraction member or at least the surface of the extraction member which is configured to contact extracted plasma or serum (or parts of said surface, e.g. at least 50%, preferably at least 70% and most preferably at least 90%) may consist of or may be coated with a material that does not adsorb and/or absorb proteins. Such material may be a material that increases hydrophylicity of the surface of the extraction member which is configured to contact extracted plasma or serum. Non-limiting examples for a hydrophilic material that may be used are polyamides (PA). Alternatively, also materials may be used that can be made hydrophilic by subsequent treatments such as polyether ether ketone (PEEK). PEEK can be made hydrophilic by chemical treatment (e.g. $O_2$ plasma treatment) or physical treatment. Accordingly, non-limiting examples for a material to be used are PA and PEEK (preferably PEEK treated to be hydrophilic).

As mentioned above, it is particularly envisaged in the context of the present invention that the extraction member is configured to extract and store plasma or serum in a liquid form. Accordingly, to increase the stability of serum or plasma and in particular the analytes therein, the device may further comprise a cooling unit, preferably a cooling unit for cooling the extraction member. To facilitate cooling of the extraction member the dimensions of the extraction member may be selected to be in the rather small ranges specified elsewhere herein. Moreover, the preferred materials from which the extraction member may be formed (e.g. plastics such as a PA or PEEK) may support fast cooling (even in absence of a cooling unit, e.g. when cooling with dry ice or cooling pads).

The device may also be configured to dry the plasma or serum after extraction. Depending on the analyte, the intended length of the storage of plasma or serum in the extraction member, or the storage temperature, it may be advantageous to configure the device to allow desiccating the plasma or serum. This may, for instance, be preferable if the device is configured for long-term storage without cooling of separated serum or plasma in the extraction member. In order to accelerate desiccating, the device may comprise a desiccation pellet. Said desiccation pellet may preferably be placed in and/or fixed to an interior part of the housing, e.g. to an interior part of the lid. The desiccation pellet used may for instance be a TBM33® (Wisepac).

The extraction member of the device according to the present invention may in principle have any shape. A preferred shape of the extraction member is a disk shape. Preferably the diameter of such disk shape is selected to be smaller than the diameter of the opening of a standard laboratory centrifugation tube, e.g. a 15 ml Falcon tube (opening diameter 15 mm), a 2 ml Eppendorf tube (opening diameter, e.g., 9 mm) or a 1.5 ml Eppendorf tube (opening diameter, e.g., 9 mm). In other words, the extraction member may be configured to fit inside of a centrifugation tube, e.g. a 15 ml Falcon tube (opening diameter 15 mm), a 2 ml Eppendorf tube (opening diameter, e.g., 9 mm) or a 1.5 ml Eppendorf tube (opening diameter, e.g., 9 mm) In particular, a disk shape with a diameter of between (about) 0.2 cm and (about) 3 cm, preferably between (about) 0.5 cm and (about) 1.8 cm, even more preferably between (about) 0.8 cm and (about) 1.5 cm, and most preferably of (about) 1.2 cm is envisaged. Selecting the diameter of the extraction member to be smaller than the diameter of the opening of a standard laboratory centrifugation tube allows placing the extraction member comprising separated serum/plasma in a centrifugation tube and therefore an easy, fast and/or gentle way to remove the extracted serum/plasma from the extraction member. In particular, no extraction step using additional liquid is required.

The extraction member may also be configured to be usable as a lid of a centrifugation tube, wherein the upper surface of the extraction member faces the interior of the centrifugation tube. Preferred centrifugation tubes in this context are a 15 ml Falcon tube (opening diameter 15 mm), a 2 ml Eppendorf tube (opening diameter, e.g., 9 mm) and a 1.5 ml Eppendorf tube (opening diameter, e.g., 9 mm) An extraction member configured to be usable as a lid of a centrifugation tube may instead of being placed in the centrifugation tube be used as a lid, wherein the upper surface of the extraction member faces the interior of the tube. Thereby, the same advantages as described above for the extraction member fitting inside a centrifugation tube are offered. An additional advantage of such configuration is that the extraction member is easy to remove from the centrifugation tube after centrifugation.

As already evident from the above, it is also envisaged that the extraction member may be configured to be detachable/removable from the remaining parts of the device according to the present invention. In other words, the extraction member may be detachably inserted into and/or fixed to the remaining parts of the device (in particular to the housing and/or the separation member and/or a sample introduction member). A removable/detachable extraction member further eases the serum/plasma removal from the extraction device, e.g. by centrifugation as described above. The extraction member may also be configured so as to be only detachable from all other parts except the housing. The housing may then be configured to receive and/or enclose the extraction member.

The separation member of the device according to the present invention may also have a disk shape, preferably also a disk shape having a diameter of between 0.2 cm and 3 cm, preferably between 0.5 cm and 1.8 cm, even more preferably between 0.8 cm and 1.5 cm, and most preferably of about 1.2 cm. The diameter and/or width of the extraction member may be as large as or larger than the diameter and/or width of the separation member. It is particularly preferred that the separation member and the extraction member both have a disk shape which may be of (substantially) the same diameter. In a top view, the separation member preferably is circumscribed (substantially or entirely) by the extraction member. This has the advantage that serum plasma can be efficiently extracted from the separation member.

The separation member of the device according to the present invention is configured to separate serum/plasma from whole blood. To separate serum/plasma from blood, the separation member may comprise or be composed of a filter (e.g. a serum/plasma separation filter) or a membrane (e.g. a serum/plasma separation membrane). Particularly preferred is that the separation member of the device according to the present invention comprises or is composed of a serum/plasma separation membrane known in the art. Accordingly, the separation member may comprise or be composed of a membrane that has an asymmetric nature, i.e. a membrane that allows the cellular components of the blood (e.g. red blood cells, white blood cells, and platelets) to be captured in the larger pores of a first portion of the membrane (e.g. the upper portion) with substantially no lysis of the cells occurring, while the plasma flows down into the smaller pores in a second portion of said membrane (e.g. the lower portion of the membrane). Alternatively, also a symmetric membrane having a defined size cut-off to retain cellular component, e.g. with a size-cut-off of 0.45 µm may be employed. Preferred separation membranes and/or plasma separation membranes that may be used in the context of the present invention are a Vivid GR membrane, a Cobetter filtration membrane and a Primecare™ membrane. The Vivid GR membrane and the Primecare™ membrane have an asymmetric nature.

The device of the present invention may further comprise a sample introduction member. Preferably, said sample introduction member may be disposed above the separation member and may be configured so that a sample (a whole blood sample) introduced via said introduction member is applied onto the separation member upper surface. The sample introduction member may be provided with one or more through holes through which the blood sample can be applied. Preferably, the introduction member has an upper surface and the one or more through holes are positioned in said upper surface. Said upper surface may be positioned substantially parallel to the separation member upper surface. The through holes may be positioned so that a sample can be applied vertically to the separation member upper surface. The number and/or position of the introduction member may be selected so as to ensure introduction of a sample in a manner to equally distribute it on the separation member upper surface. This has the advantage of a more effective separation. For instance, the introduction member may have 1 to 5, preferably 3 to 5 or most preferably 5 through holes. These through holes may be equally distributed on the introduction member upper surface.

The sample introduction member may be bonded to the separation member upper surface, preferably by an adhesive, heat and/or ultrasonic welding. Preferably, the sample introduction member is bonded to an outer perimeter of the separation member upper surface. Most preferably, the bond is mainly or even exclusively provided in said outer perimeter. It is also envisaged that a cavity or empty volume may be formed between a lower surface of the sample introduction member and the upper surface of the separation member. Such cavity or volume may prevent leakage of blood applied to the device, in particular when the applied sample volume exceeds the (temporal) volume capacity of the separation member. The cavity or empty volume may have a volume of at least (about) 10 µl to (about) 300 µl, preferably at least (about) 50 µl to (about) 200 µl, more preferably at least (about) 80 µl to (about) 150 µl and most preferably at least (about) 100 µl. Further, the cavity or empty volume may have a volume of at most (about) 300 µl, preferably at most (about) 200 µl, more preferably at most (about) 150 µl and most preferably at most (about) 100 µl.

As already mentioned above, the device of the present invention may also comprise a housing. Said housing may include a housing lid and/or a housing base. Preferably, the housing lid and the housing base may form a cavity that houses the extraction member, the separation member and/or the sample introduction member. In a closed configuration the cavity formed by the housing lid and the housing base may be liquid and/or air-tight.

Optionally, the housing lid may be configured to act as a manual pump and/or piston. Such manual pump and/or piston may be configured to be manually actuated by the user in order to increase the pressure above the separation member upper surface and/or the differential pressure across the separation member. Without wanting to be bound by theory, it is believed that increasing the pressure in this manner may accelerate the separation of blood components in the separation member and/or increase the plasma yield. For this purpose, the housing lid may be movable (e.g. slidable) with respect to the housing base, in particular towards the housing base. The housing lid may be slidable onto and/or into the housing base. In the assembled state of the device, the housing lid may, for example, be configured to be pushed towards the housing base to compress the air above the separation member. The space below the separation member may be vented, e.g. by providing a vent in the housing base.

For example, the housing lid may be configured to be a close fit with the housing base. Said fit may be substantially or entirely airtight while the space below the separation member may be vented. This may allow the user to compress the air above the separation member by pushing the housing lid towards the housing base. Alternatively or additionally, the housing lid may be provided with one or more projections (not shown) that protrude into the through holes of the sample introduction member. The projections may seal with the through holes so that the air in the sample introduction member is compressed when the housing lid is pushed towards the sample introduction member and/or towards the housing base.

The device of the present invention is preferably a device for separating plasma or serum from a rather small volume of blood. Most preferably, the device is a device for separating plasma or serum from capillary blood since capillary blood can also be gained without trained personnel and less invasively when compared to e.g. venous blood. Accordingly, the device according to the present invention may be configured to separate plasma or serum from a blood sample (e.g. a capillary blood sample) having a volume of between (about) 10 µl and (about) 300 µl, preferably between (about) 50 µl and (about) 200 µl, and more preferably between (about) 90 µl and (about) 150 µl.

The extraction member of a device of the present invention may be configured to extract and/or store at least (about) 10 µl, preferably at least (about) 20 µl, more preferably at least (about) 30 µl and most preferably at least (about) 50 µl of separated plasma or serum. Further, the extraction member of a device of the present invention may be configured to extract and/or store at most (about) 50 µl, preferably at most (about) 30 µl, more preferably at most (about) 20 µl and most preferably at most (about) 10 µl of separated plasma or serum. The volume to be extracted may, for instance, be increased by increasing the upper surface of the extraction member. Similarly, also the number, relative positioning or the height of the one or more microstructures of the extraction member may be adapted. In other words, the volume defined by the one or more channels of the extraction member may be adapted to the desired volume of serum or plasma to be extracted. The volume of serum or plasma that can be extracted may also depend on the volume capacity of separation member, because this capacity may determine how much serum or plasma can be held in the separation member and extracted therefrom. Said capacity is influenced by the separation member characteristics (asymmetric or size cut-off) and/or its dimensions (e.g. its diameter).

The extraction member of a device of the present invention may have a cavity or a volume to store the extracted serum/plasma. Said cavity or volume may, for example, be the one or more channels formed by the one or more microstructures. In other words, said volume or cavity may be formed between said one or more microstructures. The volume or cavity of the extraction member may be empty before a sample is applied to the device. It is, however, also envisaged that the extraction member (e.g. the volume to store the extracted serum/plasma) may be preloaded with a solution or a powder (e.g. a precipitate resulting from drying a solution). Using a powder or a precipitate of a solution has the advantage that the extracted serum/plasma is not diluted in the extraction member. In particular, at least (about) 5%, preferably at least (about) 10%, even more preferably at least (about) 50% of the total volume of the volume or cavity of the extraction member or of the total volume of serum or plasma intended to be stored therein may be preloaded with a solution or a precipitate (e.g. of said solution). A solution preloaded in the extraction member of the device can in principle be any solution. For instance, the solution may be a protein preservation solution. A protein preservation solution is a solution that increases the stability of one or more proteins over time, e.g. inhibits proteolysis. In the context of the present invention, it is preferred that a protein preservation solution is compatible with downstream analysis, such as mass spectrometry analysis, is used. Non-limiting examples for a protein preservation solution are surfactants and different chaotropic agents (Proc et al., doi:10.1021/pr100656u). The solution preloaded in the extraction member of the device may also be a protein preservation and/or denaturing solution comprising urea. Similarly, a preloaded powder may comprise urea, i.e. may, for example, be a precipitate resulting from drying a protein preservation and/or denaturing solution comprising urea (e.g. in the extraction member after being preloaded as a liquid). Furthermore, the extraction member may also be preloaded with stable isotope labeled versions of an analyte of interest (e.g. a stable isotope labeled protein or a peptide—e.g. a tryptic peptide—of a protein). Preferably, even a defined concentration of a stable isoptope version of an analyte of interest may be preloaded. The stable isotope labeled version of the analyte of interest may either be preloaded as solution or, alternatively, as a powder (e.g. lyophilized material). If the device is configured to separate plasma or serum for subsequent mass spectrometry analysis, for instance, one or more AQUA peptides designed for the protein(s) to be analyzed may be preloaded. A stable isotope labeled peptide (e.g. AQUA peptide) may be preloaded lyophilized or as a liquid. A liquid may also be dried, e.g. by incubation of the device or extraction member after preloading with the liquid at room temperature (e.g. for 5-60 min.).

Preloading a stable isotope labeled version of the analyte of interest allows the absolute quantification of the analyte of interest (e.g. a protein of interest) using any of the suitable targeted mass spectrometry based methods (Shi, T. et al. Advances in targeted proteomics and applications to biomedical research. *Proteomics* 16, 2160-2182, 2016). Further, this allows the device to fulfill the highest analytical validation criteria for targeted MS assays currently applied to clinical mass spectrometry (Carr, S. A. et al. Targeted peptide measurements in biology and medicine: best practices for mass spectrometry-based assay development using a fit-for-purpose approach. *Molecular & Cellular Proteomics: MCP* 13, 907-917, 2014).

The preloading of the extraction member (in particular its cavity for collecting serum or plasma) with a solution of an analyte (e.g. peptide or protein) such as with a stable isotope labeled versions of an analyte of interest (e.g. a stable isotope labeled protein or a peptide—e.g. a tryptic peptide—of a protein) may also have the advantage that the surface of the extraction member is pre-treated. By the pre-treatment parts of the surface of the extraction member that get in contact with the preloaded solution that have a certain affinity to the analyte to be analyzed are blocked/saturated before the actual sample is introduced.

Accordingly, the extraction member or at least the surface (s) of the extraction member configured (or expected) to get in contact with the separated serum/plasma may also be pre-treated, e.g. with a protein or peptide-containing solution, such as a protein or peptide-containing solution that can simultaneously be used for quantification. Alternatively, also a BSA containing solution or serum or plasma may be used for the pre-treatment. A pre-treatment with a protein-containing solution such as BSA, plasma or serum may include one or more steps of introducing a defined amount (ideally close to the total volume that can be held by the extraction member) of the protein-containing solution into the extraction member, briefly incubating (e.g. 10, 20 or 30 min) and subsequently completely removing the introduced solution (the removal step may be omitted when solutions that are simultaneously used for quantification, such as stable isotope-labeled analyte (e.g. peptide/protein) containing solutions are used). A pre-treatment (e.g. with plasma or serum or any of the above mentioned other options) may be employed when the extraction member or the parts thereof getting in contact with the separated serum or plasma are made from polyamide. A pre-treatment with a protein-containing solution or preferably serum or plasma has the purpose that surfaces of the material getting into contact with the separated serum/plasma that have a affinity to proteins and/or other analytes comprised in serum/plasma are already pre-saturated with a respective analyte from the employed pre-treatment solution such as plasma or serum. Accordingly, the pre-treatment may also be referred to as blocking.

The device of the present invention is preferably configured so that it does not require and/or comprise an external energy source that contributes to plasma or serum extraction from the separation member (beyond gravity). Gravity assures a reproducible energy source in contrast to other external energy solutions. An external energy source may in particular include any members that create pressure or suction other than the extraction member, e.g. from outside of the housing. Similarly, also members that allow manual application of an external force such as squeezing are preferably not part of the device of the present invention. Plasma or serum extraction without additional external force may in particular be achieved by using an extraction member that is configured to extract serum or plasma from the separation member by capillary forces. Moreover, the device according to the present invention may be configured so that gravity can also promote extraction from the separation member. For instance, the separation member may be positioned within the device so that gravity promotes the flow through the separation member. Accordingly, the separation member may be a vertical plasma/serum separation membrane or filter.

The device according to the present invention as described herein has inter alia the advantage that it is capable of receiving small blood volumes (e.g. fingerprick-type volumes—e.g. around 100 µl), separating the plasma/serum from the cellular components, and may store the plasma/serum in its liquid phase and preserve it for downstream molecular analysis (e.g. mass spectrometry analysis). The results shown in the appended Examples and Figures demonstrate the performance of the device in allowing the profiling of a plasma/serum proteome (more than 500 proteins reproducibly quantified) without requiring any manual intervention, thus eliminating the handling-derived analytical variability. Moreover, the appended Examples and Figures also illustrate that recovery and/or storage of serum or plasma is improved when compared to a device employing a 903 Whatman paper instead of the extraction member according to the present invention. In particular, a higher number of peptides and of certain metabolites could be measured in the serum or plasma separated and stored in the device according to the present invention. These advantageous properties and the small dimensions, the easy-to-use principle, the economic fabrication process and the lack of external energy for its function make the device according to the present invention suitable for future point of care applications.

According to a second aspect, the present invention relates to a method for separating plasma or serum from a blood sample. The method preferably comprises the steps of:
a) providing a device for separating serum or plasma from blood according to the present invention (as described herein);
b) introducing the blood sample in said device; and
c) separating the plasma or serum (e.g. by waiting for a predetermined period of time).

The blood sample employed in the context of the method of the present invention may in principle be any blood sample suitable to gain serum or plasma therefrom. Preferably, the sample is fresh blood, such as venous blood or capillary blood. Most preferably, the blood sample is capillary blood.

In step b) mentioned above the blood sample may be applied drop-wise to the device. For instance, capillary blood, which is typically gained drop-wise, may be applied in drops. If the device comprises more than one through holes (e.g. in the introducing member of the device) through which the blood can be applied and more than one drop of blood is applied in step b), the blood is preferably applied to different of said one or more through holes (e.g. in the introducing member of the device) in order to equally distribute the blood sample on the separation member of the device.

In step c) of the method of a present invention as mentioned above, the device may be stored and/or incubated. The storage or incubation may be performed for at least 2 min, preferably at least 5 min, and more preferably at least 10 min. In other words, the predetermined period of time waited in order to separate plasma or serum after applying a blood sample to the device (i.e. after step b)) may be at least 2 min, preferably at least 5 min, and more preferably at least 10 min. Furthermore, in step c) the device may be stored and/or incubated for at most 20 min, preferably at most 15 min, and more preferably at most 10 min. In other words the predetermined period of time waited in order to separate plasma or serum after applying a blood sample to the device (i.e. after step b)) may be at most 20 min, preferably at most 15 min, and more preferably at most 10 min. The incubation or storage step besides separation of the plasma/serum from the blood may also comprise extraction of the separated plasma/serum from the separation member of the device to the extraction member of the device.

The method for separating plasma or serum from a blood sample may further comprise storing the extracted plasma or serum in the device and/or in the extraction member for at least 1 day, preferably at least 2 days, more preferably at least 5 days and most preferably at least 10 days after step c). Said storage may be conducted at a temperature of between 0° C. to 50° C., preferably between 10° C. to 40° C. or most preferably between 15° C. and 25° C. In particular, said storage may also be conducted at room temperature (e.g. at (about) 20° C.). Storage at room temperature is very convenient and also less expensive than storing a sample in the cold. Moreover storage at room temperature also allows for shipment of a serum or plasma sample in places without access to cold preservation solution (e.g. dry ice, ice pack). This may be of particular relevance for personalized medicine uses.

It is also envisaged that said storage is conducted at a temperature of 2° C. to 8° C., 3° C. to 6° C., or at (about) 4° C. The storage step may also be conducted at lower temperatures such as −80° C. to −10° C. In particular, the separated serum or plasma may be shock frozen, e.g. in liquid nitrogen or dry ice. Storage in a frozen state may, for example, increase stability of certain analytes. Storage in a frozen state and/or shock freezing may in particular be employed when it is envisaged to analyze an analyte which is known to have low stability at room temperature or when no preservation solution that could be preloaded in the extraction member is known for an analyte. For instance, such analyte may be a metabolite.

According to the present invention, the method for separating plasma or serum from a blood sample may also comprise a step of transferring the separated plasma or serum from the extraction member of the device to a separate tube, e.g. a centrifugation tube (e.g. a 15 ml Falcon tube, a 2 ml Eppendorf tube or a 1.5 ml Eppendorf tube). Said transferring step may include placing the extraction member of the device in a centrifugation tube and transferring the plasma or serum from the extraction member of the device to said centrifugation tube by centrifugation. It is particularly preferred that the extraction member can be taken out and/or detached from the device and that only the extraction member is placed in the centrifugation tube. However, although less preferred, also the whole device may be placed in a centrifugation tube. Further, if a device having a extraction member is configured to be usable as lid of a centrifugation tube, wherein the extraction member upper surface faces the interior of the centrifugation tube, the extraction member may instead of being placed in the centrifugation tube also be placed on the centrifugation tube. The centrifugation to transfer the separated plasma or serum from the extraction member to the centrifugation tube may be conducted at, for example, (about) 500 to (about) 3000 rpm for (about) 10 to (about) 120 seconds.

According to a third aspect, the present invention also relates to a method for analyzing one or more analytes (preferably proteins and/or metabolites) contained in plasma or serum separated from a blood sample. The method for analyzing one or more analytes contained in plasma or serum may be a method for analyzing one or more proteins. Similarly, the method for analyzing one or more analytes contained in plasma or serum may also be a method for analyzing one or more a metabolites. Any of said methods may comprise:

a) separating plasma or serum from a blood sample using a device for separation of plasma or serum from blood according to the present invention as described herein; and b) analyzing the one or more analytes (e.g. proteins and/or metabolites) in the separated plasma or serum.

Step a) of the method for analyzing one or more analytes (e.g. proteins and/or metabolites) mentioned-above preferably comprises or is any one of the methods for separating plasma or serum from a blood sample as described herein elsewhere.

The one or more analytes (e.g. proteins or metabolites) to be analysed may be predetermined or targeted, i.e. it may be known before which analyte(s) (e.g. protein(s) and/or metabolite(s) are to be analysed (e.g. by using antibody-based methods or targeted mass spectrometry). Alternatively, said one or more analytes (e.g. proteins or metabolites) may not be predetermined, i.e. the plasma or serum may be generally analyzed for analyte content (e.g. protein and/or metabolite content). To this end, for instance, untargeted mass spectrometry may be used when protein and/or metabolite content is determined.

The one or more analytes to be analyzed may be in principle any kind of analytes present in plasma or serum that can be detected. These analytes may, for example, be parasites, viruses, cell free DNA, proteins and/or metabolites. Depending on the analytes to be detected a skilled person will know which analysis method can be employed in step b). As indicated above, most preferably, the one or more analytes to be analyzed are one or more proteins and/or one or more metabolites. The one or more proteins and/or metabolites may for example be biomarkers. Preferred proteins to be analyzed are: Ovarian cancer biomarkers (e.g. as described in Huttenhain, R. et al. Reproducible quantification of cancer-associated proteins in body fluids using targeted proteomics. *Science translational medicine* 4, 142ra194 (2012)), the FDA-approved OVA@ biomarker panel (including e.g. B2MG, APOA1, TTHY and TRFE) or any one of CRP, ApoA1, Albumin and IGF-1, or any one of IGF1, ADIPOQ, GP1BA and CBPB2). Similarly, preferred proteins may be the proteins as detected in the appended Examples and Figures. The appended Examples and Figures illustrate that separation of serum or plasma with the device according to the present invention having an extraction member as described herein is highly efficient and allows detection of hundreds of proteins in subsequent mass spectrometry analysis. Importantly, the device according to the present invention having an extraction member with microstructures (e.g. micro-pillars) as described herein is shown to be more efficient in total peptide recovery than a similar device employing a 903 Whatman paper instead. Examples for metabolites to be analyzed are: Acylcarnitines, Amino acids and/or Biogen amines, Lysophatidylcholines, Phosphatidylcholines, Sphingomyelins and/or Monosaccharides. As illustrated in the appended Examples and Figures, using the device according to the present invention for separation of plasma or serum from blood allows recovering metabolites efficiently, i.e. allows robust detection of dozens of metabolites. In particular, the appended Examples and Figures illustrate that some metabolites are recovered even more efficiently with the device according to the present invention having the extraction member as described herein than with a device using a 903 Whatman paper instead. These metabolites include Acylcarnitines and Phosphatidylcholines. Accordingly, the one or more analytes may be selected from the group consisting of Acylcarnitines and Phosphatidylcholines. Non-limiting examples of biomarkers including proteins and metabolites to be analyzed are also mentioned in the appended Examples and Figures.

Step b), analyzing the one or more analytes (proteins and/or metabolites) in the separated plasma or serum, as mentioned-above may for instance mean determining the amount of an analyte (e.g. protein and/or metabolite (e.g. a biomarker)). It may however, also encompass detecting processed or modified forms of an analyte. This may in case of a protein be proteolysis or the detection of posttranslational modifications (e.g. phosphorylation, modification with ubiquitin or a ubiquitin-like modifier, glycosylation, acetylation, methylation, etc.). In other words, analyzing one or more proteins or metabolites may be any of the above mentioned.

The method of analyzing one or more proteins and/or metabolites in plasma or serum may also encompass performing step a) for several (two or more) blood samples of the same individual and subsequently in step b) analyzing one or/more proteins in the separated serum of the samples. The method may further comprise comparing results, e.g. comparing the amounts and/or any of the other modification (s) or post-translational modification(s).

The several blood samples employed may be blood samples of different time points (e.g. two) and may thus allow for predicting the course of a disease identified based on the respective amount(s), modification(s) and/or post-translational modification(s) of the analyzed analytes (e.g. protein(s) and/or metabolite(s)).

In the context of the present invention in principle any method suitable for analyzing analytes (e.g. proteins or metabolites) may be employed. Such methods are well known in the art and may be selected dependent on the analyte. In particular, it is envisaged that analyzing one or more proteins or metabolites involves proteomic-based methods, preferably mass spectrometry. Mass spectrometry and other proteomic-based methods have the advantage that they allow simultaneous detection of many proteins and/or metabolites. This allows analyzing changes in the proteome and/or metabolome of an individual on a more general manner than most of the current antibody-based analyses (immunoassays) such as ELIS A-like tests.

The method according to the third aspect of the present invention may also comprise storing the separated plasma or serum in the extraction member of the device employed in step a) as defined above. The separated plasma or serum may in particular also be stored as a liquid in the extraction member between steps a) and b). To this end, preferably an extraction member having a surface being in contact with the separated serum or plasma that allows for storage as a liquid, as defined further above in the context of the first aspect of the present invention, is employed in step a) of the method. If the serum or plasma is stored as a liquid in the extraction member of the device between steps a) and b), it is preferred to store the serum or plasma at a temperature between 0° C. to 50° C., preferably between 10° C. to 40° C. or most preferably between 15° C. and 25° C. It is also envisaged that said storage is conducted at a temperature of 2° C. to 8° C., more preferably 3° C. to 6° C. and most preferably at (about) 4° C. As mentioned above, the extraction member may be preloaded with a protein preservation and/or denaturing solution. Even more preferably in the context of storage of plasma or serum as a liquid (e.g. at any of the temperatures indicated above, preferably at 4° C. for at least or exactly two days), the extraction member may be preloaded with and/or comprise a powder such as the precipitate of a protein preservation and/or denaturing solution, i.e. a dried protein preservation and/or denaturing solution (e.g. by evaporation of the liquid, such as by incubation at room temperature until all liquid is evaporated). The protein preservation and/or denaturing solution or the powder preferably comprises urea (e.g. may be a urea-based denaturation solution or powder). Applying urea-containing solutions or powders are particularly suited for storing serum or plasma for subsequent analysis of proteins and/or metabolites. Alternatively, depending on the analyte to be analyzed the serum or plasma may also be shock frozen (e.g. in liquid nitrogen or dry ice), e.g. if beneficial for analyte stability. Also it is preferable to store the liquid plasma using protein denaturing and/or protein preservation solutions/agents (e.g. as mentioned elsewhere herein). The storage may be performed for at least 1 day, preferably at least 2 days, more preferably at least 5 days and most preferably at least 10 days. The advantages of storing plasma or serum as a liquid have been discussed herein further above. These advantages are of particular importance in the present method since analyzing in step b) typically requires serum or plasma in a liquid form. Accordingly, a resolubilization or extraction step from material it is adsorbed to would otherwise be required. In other words, no step of extracting proteins and/or metabolites from the extraction member of the device according to the present invention with a liquid (e.g. water) is required. As mentioned above, this may minimize loss or unequal extraction when compared to the solutions provided in, e.g., US 2012/0024788 A1.

In some settings, e.g. if storage without cooling (e.g. at room temperature) is desired, the method according to the third aspect may also comprise between steps a) and b):
  i) Desiccating the separated plasma or serum in the extraction member (e.g. by a desiccation pellet in the device for separating plasma or serum); and
  ii) Dissolving the desiccation product resulting from step i) in an aqueous solution (e.g. directly before step b)).

The method may optionally further comprise storing the serum or plasma pellet resulting from desiccation in step i) between step i) and ii) for at least 24 h, preferably at least 36 h and most preferably at least 48 h. The storage can be performed at any temperature between −80° C. and 37° C., but is preferably performed at room temperature (e.g. between 20° C. to 25° C.).

The desiccation in step i) may last for 10 to 40 min per 15 μl plasma or preferably for 20-30 min per 15 μl plasma or serum.

It is particularly also envisaged to combine desiccation and preloading of the extraction member with a storage or preservation solution and/or a powder (e.g. comprising urea) as described above.

The present invention in particular also relates to the following aspects:

1. A device for separation of plasma or serum from a blood sample, wherein said device comprises:
   an optional housing,
   a separation member configured to separate plasma or serum from cellular blood components by retaining said cellular components of blood, wherein said separation member preferably has a separation member upper surface and an opposing separation member lower surface, wherein said separation member upper surface or a portion thereof preferably is configured to receive a blood sample, and
   an extraction member for extracting the separated plasma or serum from the separation member,
   wherein the extraction member preferably comprises or consists of a base and one or more microstructures that may protrude from and/or may be integrally formed with said base, preferably wherein the upper surface of said one or more microstructures forms an extraction member upper surface, and preferably wherein said one or more microstructures are configured to extract plasma or serum from said separation member by capillary forces.
2. The device of aspect 1, wherein said extraction member is disposed below said separation member.
3. The device of aspect 1 or 2, wherein said extraction member upper surface is in contact with said separation member lower surface, preferably in intimate contact.
4. The device of aspect 3, wherein at least 50%, at least 60%, at least 80%, or at least 90% of said extraction member upper surface are in contact with the separation member lower surface.
5. The device of any preceding aspect, wherein said extraction member is further configured to collect and/or store the plasma or serum extracted from the separation member.
6. The device of any preceding aspect, wherein said one or more microstructures have a height of 0.1 mm to 1 mm, preferably of 0.2 mm to 0.7 mm, even more preferably 0.3 mm to 0.5 mm and most preferably of 0.3 mm
7. The device of any preceding aspect, wherein the device comprises a plurality of microstructures, and wherein the upper surfaces of the plurality of microstructures form said extraction member upper surface.
8. The device of aspect 7, wherein said plurality of microstructures are micro-pillars.
9. The device of aspect 8, wherein
   the micro-pillars have a substantially rectangular cross section;
   the micro-pillars have a length of 0.2 mm to 3 mm, preferably 0.5 mm to 2 mm, more preferably 0.8 mm to 1.2 mm and most preferably about 1 mm; and
   the micro-pillars have a width of 0.1 mm to 1.5 mm, preferably 0.2 mm to 1 mm, more preferably 0.3 mm to 0.8 mm and most preferably about 0.5 mm
10. The device of aspect 8, wherein
    the micro-pillars have a substantially triangular, quadrilateral, rectangular or square cross section; and
    the side length of said cross section is between 0.2 mm and 3 mm, preferably between 0.5 mm and 2 mm, more preferably between 0.8 mm and 1.2 mm, and most preferably about 1 mm
11. The device of aspect 8, wherein
    the micro-pillars have a substantially circular cross section; and
    the diameter of said cross section is between 0.2 mm and 3 mm, preferably between 0.5 mm and 2 mm, more preferably between 0.8 mm and 1.2 mm, and most preferably about 1 mm
12. The device of any preceding aspect, wherein
    the extraction member is provided with one or more channels, preferably a plurality of channels; and
    the one or more channels are formed by the base in conjunction with the one or more microstructures.
13. The device of aspect 12, wherein the median opening width of said one or more channels at the extraction member upper surface in a top view of said extraction member is between 0.1 mm and 2 mm, preferably between 0.3 mm and 1.2 mm, more preferably between 0.4 mm and 0.6 mm, and most preferably about 0.5 mm
14. The device of aspect 12 or 13, wherein, in a top view of the extraction member:
    the one or more channels define a total channel length; and
    the opening width of said one or more channels at the extraction member upper surface is at least 1 mm, preferably at least 0.7 mm, and more preferably at least 0.5 mm along at least 50%, at least 60%, at least 70%, at least 80%, or at least 90% of said total channel length.
15. The device of aspect 12, 13 or 14, wherein, in a top view of the extraction member:
    the one or more channels define a total channel length; and
    the opening width of said one or more channels at the extraction member upper surface is at most 1 mm, preferably at most 0.7 mm, and more preferably at most 0.5 mm along at least 50%, at least 60%, at least 70%, at least 80%, or at least 90% of said total channel length.
16. The device of any preceding aspect, wherein the median distance between adjacent microstructures is between 0.1 mm and 2 mm, preferably between 0.3 mm and 1.2 mm, more preferably between 0.4 mm and 0.6 mm, and most preferably about 0.5 mm.
17. The device of any preceding aspect, wherein at least 50%, at least 60%, at least 70%, at least 80%, or at least 90% of adjacent microstructures are arranged with a distance there between of 1.5 mm to 0.2 mm, preferably 1 mm to 0.35 mm, and more preferably 0.75 mm to 0.5 mm
18. The device of any preceding aspect, wherein said one or more microstructures protrude perpendicular from said base.
19. The device of any preceding aspect, wherein
    the extraction member has an extraction member lower surface; and
    the extraction member lower surface is at least one of: continuous, non-porous, non-perforated and/or impermeable to plasma or serum.
20. The device of any preceding aspect, wherein
    the base is a base plate; and the base plate preferably is a solid, rigid, self-supporting and/or unitary.
21. The device of any preceding aspect, wherein
the one or more microstructures are solid, rigid and/or self-supporting; and/or
wherein said one or more microstructures are formed from the same material than the base.
22. The device of any preceding aspect, wherein said base plate has a thickness of between 0.2 mm and 2 mm, preferably between 0.5 mm and 1.5 mm, and even more preferably between 0.8 mm and 1.2 mm
23. The device of any preceding aspect, wherein said extraction member is made from a plastic, photoresist resin or any polymeric material.
24. The device of any preceding aspect, wherein said extraction member is made from polyamide preferably nylon, polyether ether keton, acrylic or acrylic-derivatives such as poly(methyl methacrylate), Cyclic Olefin Copolymer, or epoxy SU-8.
25. The device of any preceding aspect, wherein said extraction member and/or separation member has a disk shape, preferably a disk shape having a diameter of between 0.2 cm and 3 cm, preferably between 0.5 cm and 1.8 cm, even more preferably between 0.8 cm and 1.5 cm, and most preferably of about 1.2 cm.
26. The device of any preceding aspect, wherein said extraction member is configured to be used as a lid of a centrifugation tube, wherein the upper surface of the extraction member faces the interior of the centrifugation tube.
27. The device of any preceding aspect, wherein said extraction member is configured to fit inside of a centrifugation tube.
28. The device of any preceding aspect, wherein said extraction member does not comprise or is not a membrane or a filter.
29. The device of any preceding aspect, wherein said separation member is a separation membrane, preferably a plasma separation membrane.
30. The device of aspect 28, wherein said separation membrane or said plasma separation membrane is selected from the group consisting of a Vivid GR membrane, Cobetter filtration membrane and Primecare™ membrane.
31. The device of any preceding aspect, wherein the device further comprises a sample introduction member, said sample introduction member being disposed above the separation member and having a configuration that allows the sample to be applied onto the separation member upper surface.
32. The device of aspect 31, wherein said sample introduction member is provided with one or more, preferably 1 to 5, through holes through which the blood sample can be applied.
33. The device of aspect 31 or 32, wherein the sample introduction member is bonded to the separation member upper surface, preferably by an adhesive, heat and/or ultrasonic welding.
34. The device of aspect 33, wherein the sample introduction member is bonded to an outer perimeter of the separation member upper surface, preferably wherein the bond is exclusively provided in said outer perimeter.
35. The device of any one of aspects 31 to 34, wherein a cavity is formed between a lower surface of the sample introduction member and the upper surface of the separation member.
36. The device of aspect 35, wherein said cavity has a volume of at least 10 µl to 300 µl; preferably at least 50 µl to 200 µl, more preferably at least 80 µl to 150 µl and most preferably at least 100
37. The device of aspect 35 or 36, wherein said cavity has a volume of at most 300 µl; preferably at most 200 more preferably at most 150 µl and most preferably at most 100 µl.
38. The device of any preceding aspect, wherein the housing comprises:
a housing lid; and
a housing base; and
wherein said housing lid and said housing base form a cavity that houses the extraction member, the separation member and/or the sample introduction member.
39. The device of any preceding aspect, wherein said device is configured to separate plasma or serum from blood samples having a volume of between 10 µl and 300 µl, preferably between 50 µl and 200 µl, and more preferably between 90 µl and 150 µl.
40. The device of any preceding aspect, wherein said extraction member is configured to extract and/or store at least 10 µl, preferably at least 20 µl, more preferably at least 30 µl and most preferably at least 50 µl of separated plasma or serum.
41. The device of any preceding aspect, wherein said extraction member is configured to extract and/or store at most 50 µl, preferably at most 30 µl, more preferably at most 20 µl and most preferably at most 10 µl of separated plasma or serum.
42. The device of any preceding aspect, wherein said extraction member is preloaded with a solution or a precipitate resulting from drying said solution.
43. The device of any one of aspect 42, wherein said solution that is preloaded in the extraction member comprises 5%, preferably 10%, even more preferably 50% of the total volume that can be stored in the extraction member.
44. The device of aspect 42 or 43, wherein said solution is a protein or metabolite preservation solution.
45. The device of any preceding aspect, wherein the surface of the extraction member which is configured to contact extracted plasma or serum consists of or is coated with a material that does not absorb proteins, preferably with a material that increases hydrophylicity of the surface of the extraction member which is configured to contact extracted plasma or serum.
46. The device of any preceding aspect, wherein said device does not require and/or comprise an external energy source that contributes to plasma or serum extraction from said separation member.
47. A method for separating plasma or serum from a blood sample, wherein said method comprises the steps of:
a) providing a device according to one of the preceding aspects;
b) introducing the blood sample; and
c) separating the plasma or serum by waiting for a predetermined period of time.
48. The method of aspect 47, wherein the blood sample of step b) is fresh blood, preferably capillary blood.
49. The method of aspect 47 or 48, wherein in step b) said blood sample is applied drop-wise to the device.
50. The method of any one of aspects 47 to 49, wherein in step c) the device is stored and/or incubated for at least 2 min, preferably at least 5 min, and more preferably at least 10 min 51. The method of any one of aspects 47 to 50, wherein in step c) the device is stored and/or incubated for at most 20, preferably at most 15, and more preferably at most 10 min.
52. The method of any one of aspects 47 to 51, wherein said method further comprises storing the extracted plasma or serum in the device and/or in the extraction member for at least 1 day, preferably at least 2 days, more preferably at least 5 days and most preferably at least 10 days, preferably at room temperature.
53. The method of any one of aspects 47 to 52, wherein said method further comprises a step of transferring the separated plasma or serum from the extraction member to a separate tube.
54. The method of aspect 53, wherein said transferring comprises:
    placing the extraction member in a centrifugation tube; and
    transferring the plasma or serum from the extraction member to the centrifugation tube by centrifugation.
55. A method for analyzing one or more proteins and/or metabolites contained in plasma or serum separated from a blood sample, the method comprising:
    a) separating plasma or serum from a blood sample using a device as defined in any one of aspects 1 to 46, preferably with a method as defined in any one of aspects 47 to 54;
    b) analyzing said one or more proteins and/or metabolites in the separated plasma or serum.
56. The method of aspect 55, wherein said one or more proteins and/or metabolites are biomarkers.
57. The method of aspect 55 or 56, wherein step b) involves a proteomic based method including a mass spectrometry based method.
58. The method of any one of aspects 55 to 57, wherein between step a) and step b) no step for extraction of proteins from the extraction member of the device involving addition of a liquid is required.
59. The method of any one of aspects 55 to 57, wherein the method comprises between steps a) and b):
    i) desiccating the separated plasma or serum in the extraction member;
    ii) dissolving the desiccation product resulting from step i) in an aqueous solution.
60. The method of aspect 59, wherein said method further comprises storing a desiccation pellet resulting from step i) between step i) and ii) for at least 24 h, preferably at least 36 h and most preferably at least 48 h.
61. The method of aspect 60, wherein said storing is performed at room temperature.
62. The method of any of aspects 59 to 61, wherein the plasma or serum is desiccated for 10 to 40 min, preferably for 20-30 min per 15 µl plasma or serum using one or more desiccation pellets.

The invention will be described in more detail with reference to the figures below. These figures disclose embodiments of the invention for illustrational purposes only. In particular, the disclosure provided by the figures is not meant to limit the scope of protection conferred by the invention.

FIGS. 1A-1I Schematic drawings of a preferred embodiments of plasma/serum separator devices according to the present invention.

Figure 2A:
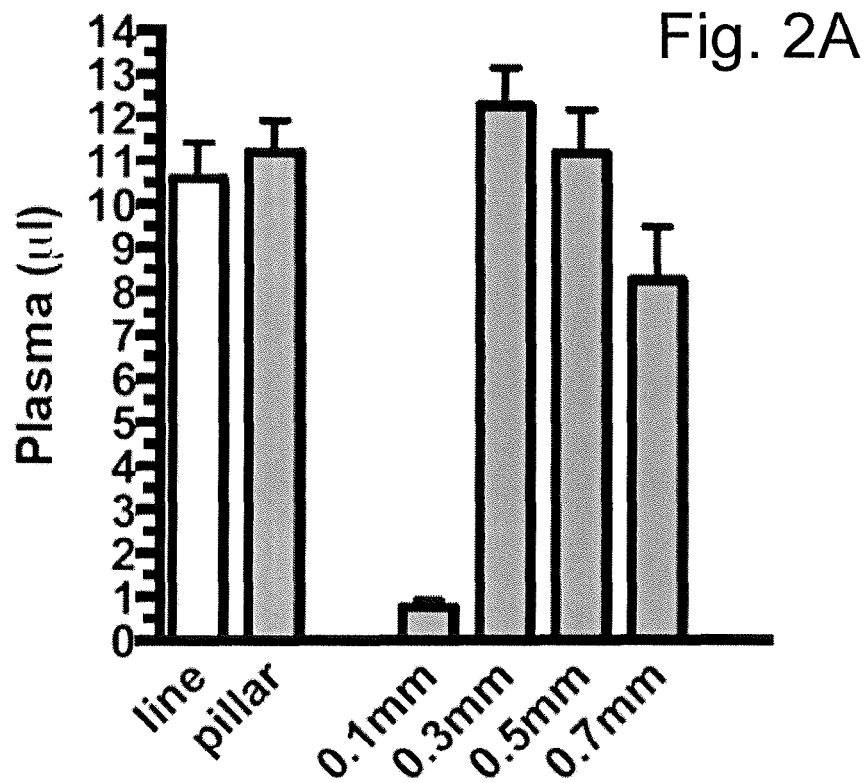
Figure 2B:
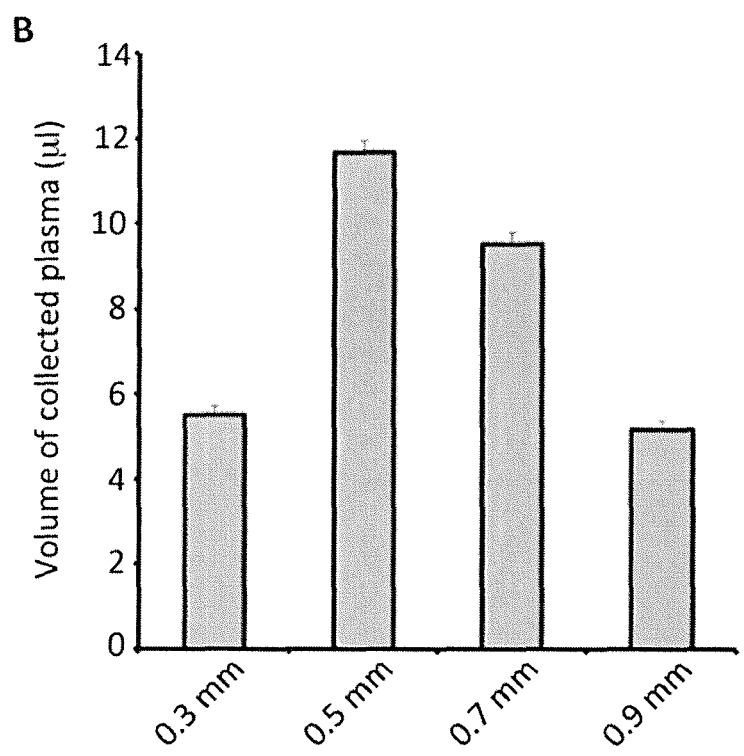
Figure 2C:
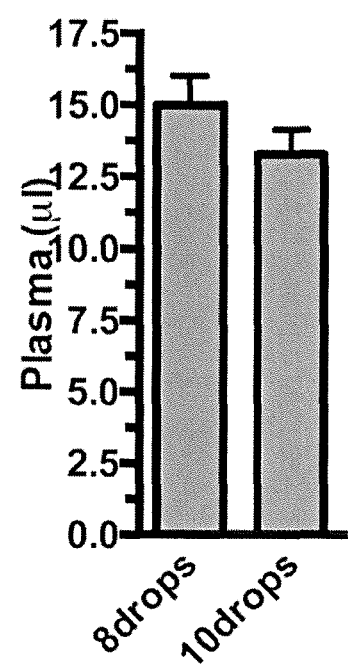

FIGS. 2A-2C Volume of plasma extracted and stored in extraction members (all experiments used discs formed from polyacrylamide (PA) with different microstructure patterns). In FIG. 2A, the first two bars on the left represent discs with either line-like microstructures (i.e. micro-pillars that extend over the whole length of the disc extraction member; indicated as white bar; indicated as "line" in the figure) or micro-pillars (grey bar; indicated as "pillar" in the figure). In both cases, the microstructures were 0.5 mm high, had a width of 0.5 mm, and a spacing between adjacent microstructures of 0.5 mm. The micro-pillars had a length of 1 mm. The four bars on the right represent volumes extracted when varying the height of the micro-pillars. In FIG. 2B, the bars represent the volumes extracted when using extraction member discs with varying widths between the micro-pillars. The height of the micro-pillars was 0.5 mm FIG. 2C shows amounts of plasma extracted into the PA extraction member discs when different volumes of human capillary blood were applied by a volunteer user.

Figure 3:
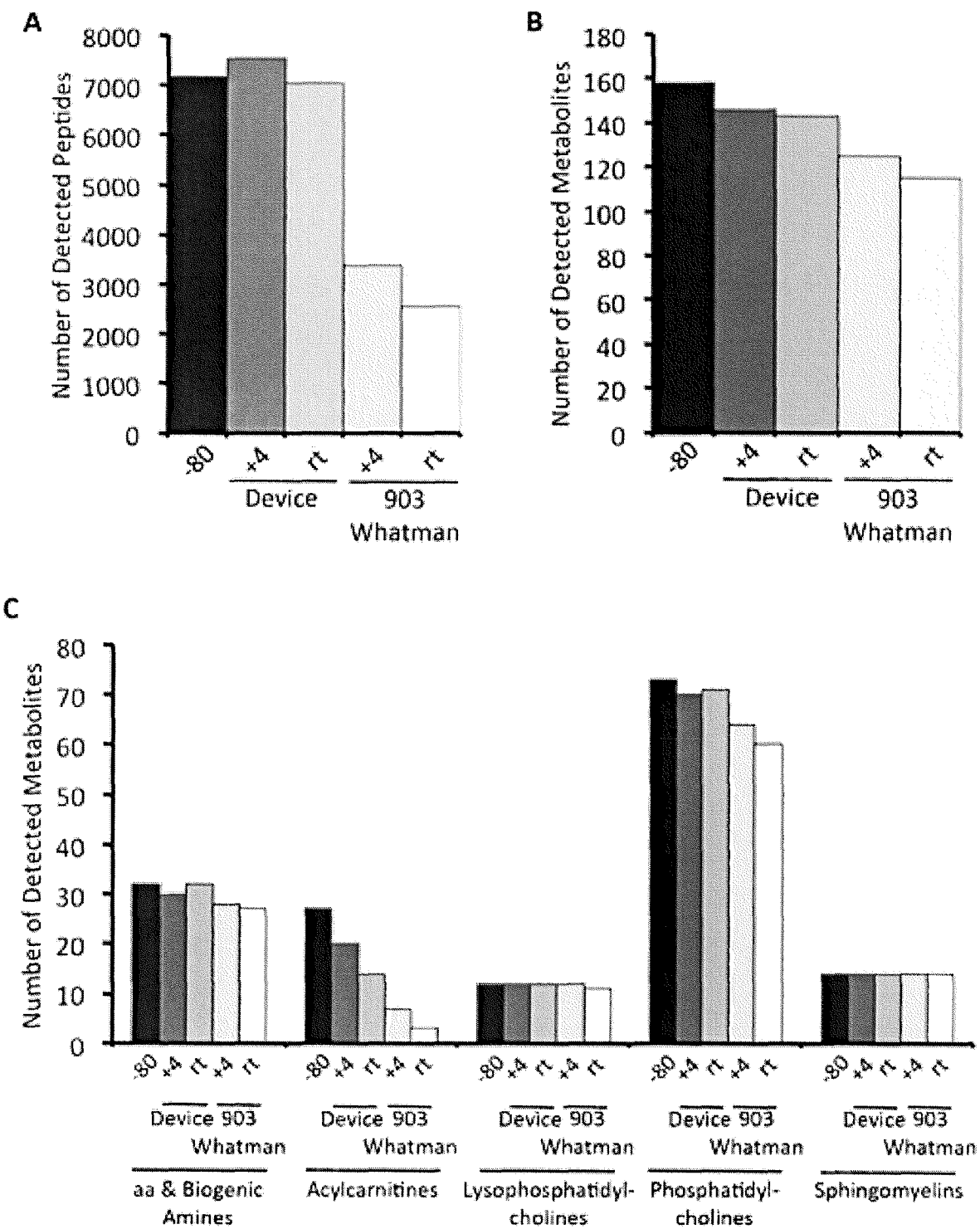

FIGS. 3A-3C Preservation/Sample Storage ability of the device of the present invention. In FIG. 3A, the number of peptides detected using data-independent-acquisition (DIA) mass spectrometry in the different plasma samples is shown. Plasma samples were obtained with the device of the present invention (having an extraction member with micropillars with a high of 0.5 mm, a width of 0.5 mm, a length of 1 mm and a spacing between adjacent micro-pillars of 0.5 mm) and preserved/stored at +4° C. ("+4" in FIG. 3A) or room temperature ("rt" in FIG. 3A) inside the device of the present invention (referred to as "Device" in the FIG. 3A) or for comparison with a device using a 903 Protein Saver paper (referred to as "903 Whatman" in the FIG. 3A) as extraction member. The samples obtained with the device using a 903 Protein Saver paper (903 Whatman) were stored in the 903 Protein Saver paper as described in the Examples. In FIG. 3B, the number of metabolites detected using an AbsoluteIDQ p180k Biocrates metabolomic mass spectrometry kit in the different samples is shown. Plasma was obtained by the device of the present invention (see FIG. 3A) and preserved at +4° C. ("+4" in FIG. 3B) or room temperature ("rt" in FIG. 3B) inside the device of the present invention (referred to as "Device" in FIG. 3B) or for comparison with a similar device using a 903 Protein Saver paper (referred to as "903 Whatman" in FIG. 3B) as extraction member. The samples obtained with the device using a 903 Protein Saver paper (903 Whatman) were stored in the 903 Protein Saver paper as described in the Examples. In FIG. 3C, the number of metabolites (classified in chemical types) were detected using an AbsoluteIDQ p180k Biocrates metabolomic mass spectrometry kit in the different samples. Plasma was obtained by the device of the present invention (as in FIG. 3A) and preserved at +4° C. ("+4" in FIG. 3C) or room temperature ("rt" in FIG. 3C) inside the device of the present invention (referred to as "Device" in the FIG. 3C) or for comparison in a similar device using a 903 Protein Saver paper (referred to as "903 Whatman" in FIG. 3C). The samples obtained with the device using a 903 Protein Saver paper (903 Whatman) were stored in the 903 Protein Saver paper as described in the Examples. In all cases (FIGS. 3A to 3C) the results are compared with the results from a sample where capillary plasma was obtained by centrifugation of capillary blood (10 minutes at 2500 rpm at +4° C.) and stored immediately at −80° C. ("−80" in the figures). The experiments using 903 Whatman as extraction member were performed by placing the paper below and in contact with the separation membrane (therefore, in substitution of the micro-pillar extraction member). After 10 minutes, the paper was removed from the device, dried at room temperature for 30 minutes and stored in light-protected bags including a desiccant.

Figure 4A:
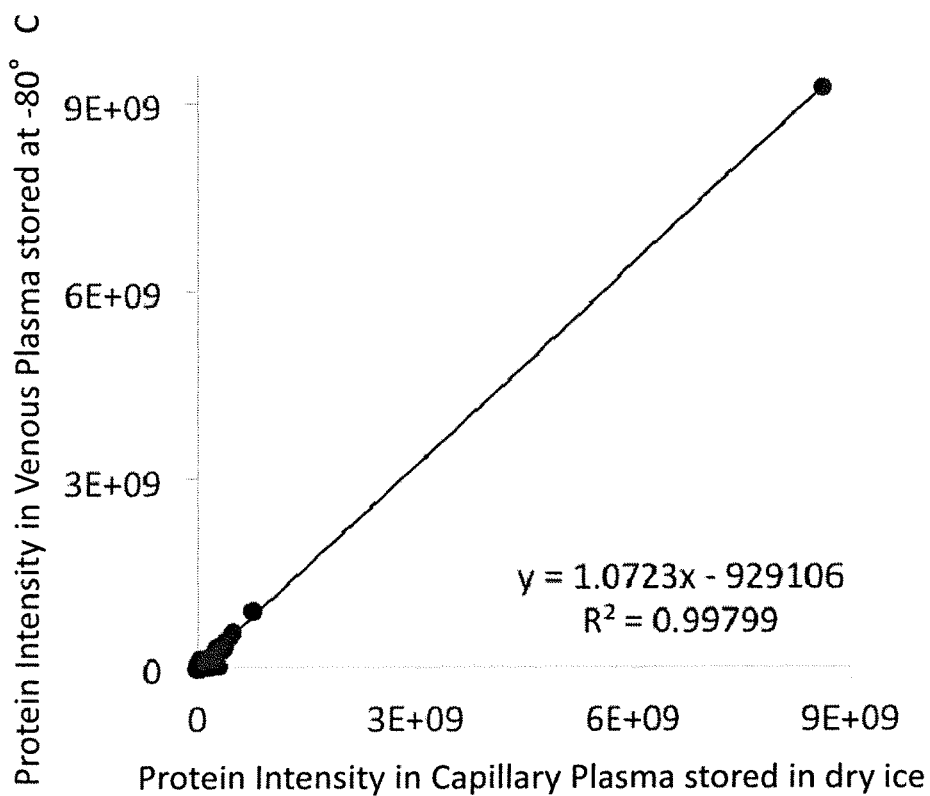
Figure 4B:
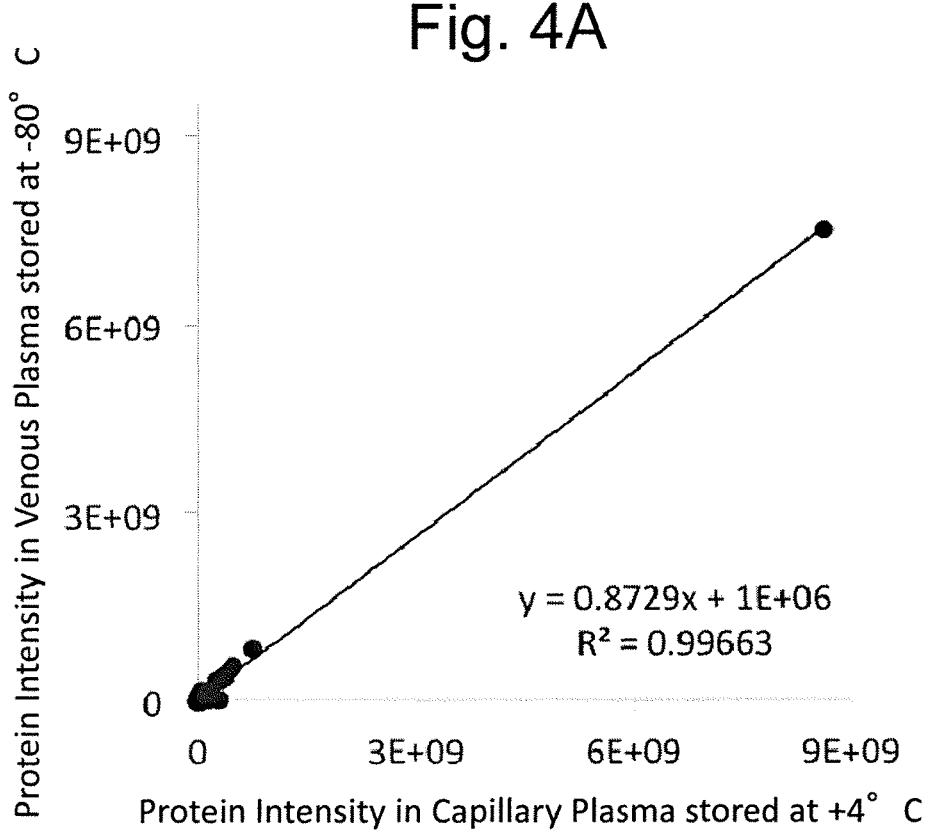
Figure 4C:
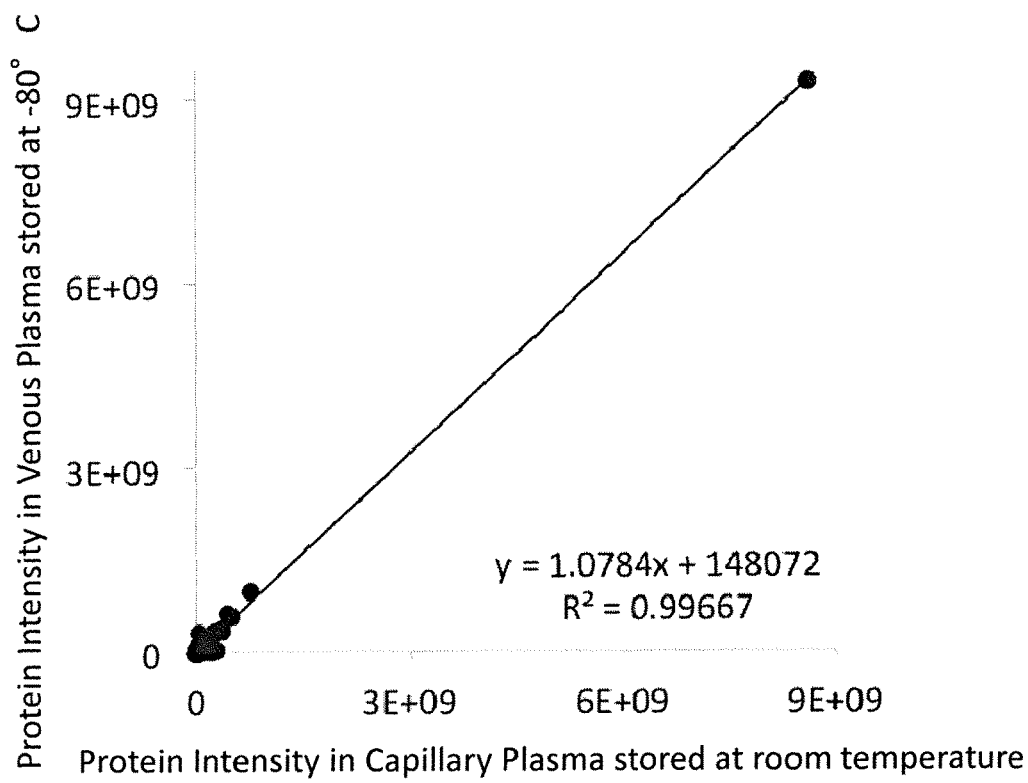

FIG. 4A-4C DIA-type mass spectrometry-derived intensity values for 511 proteins (each protein is represented by a circle) in a control venous human plasma sample obtained by classical centrifugation of venous blood (10 minutes at 2500 rpm at +4° C.) and stored immediately at −80° C. (y axes), compared to the intensity in capillary human plasma samples (x axes) obtained with a device according to the present invention as shown in FIG. 1 and stored in dry ice (FIG. 4A), +4° C. (FIG. 4B), and at room temperature (FIG. 4C), in each case for 48 hours.

Figure 5A:
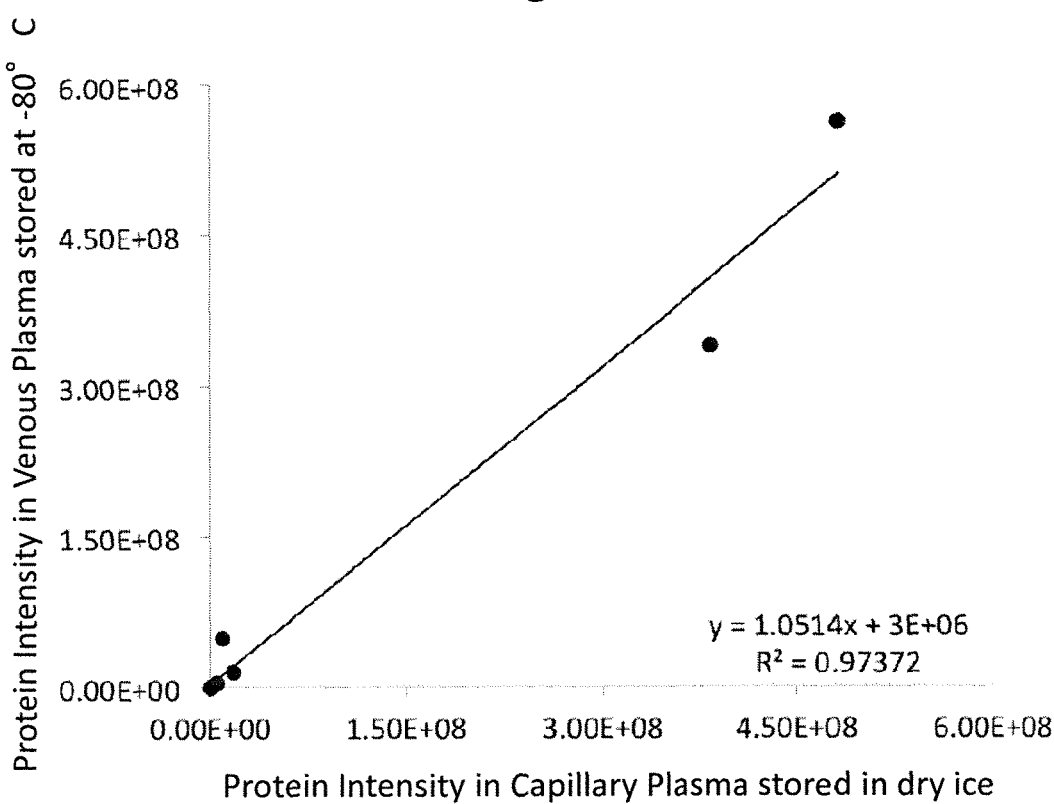
Figure 5B:
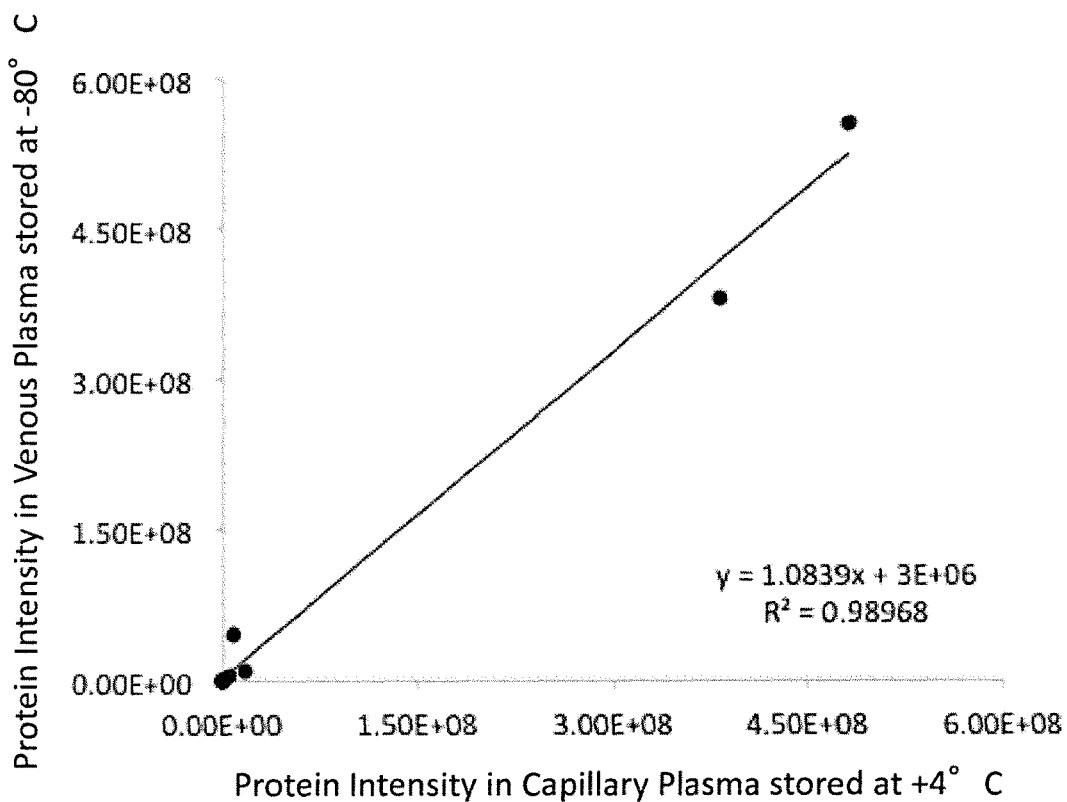
Figure 5C:
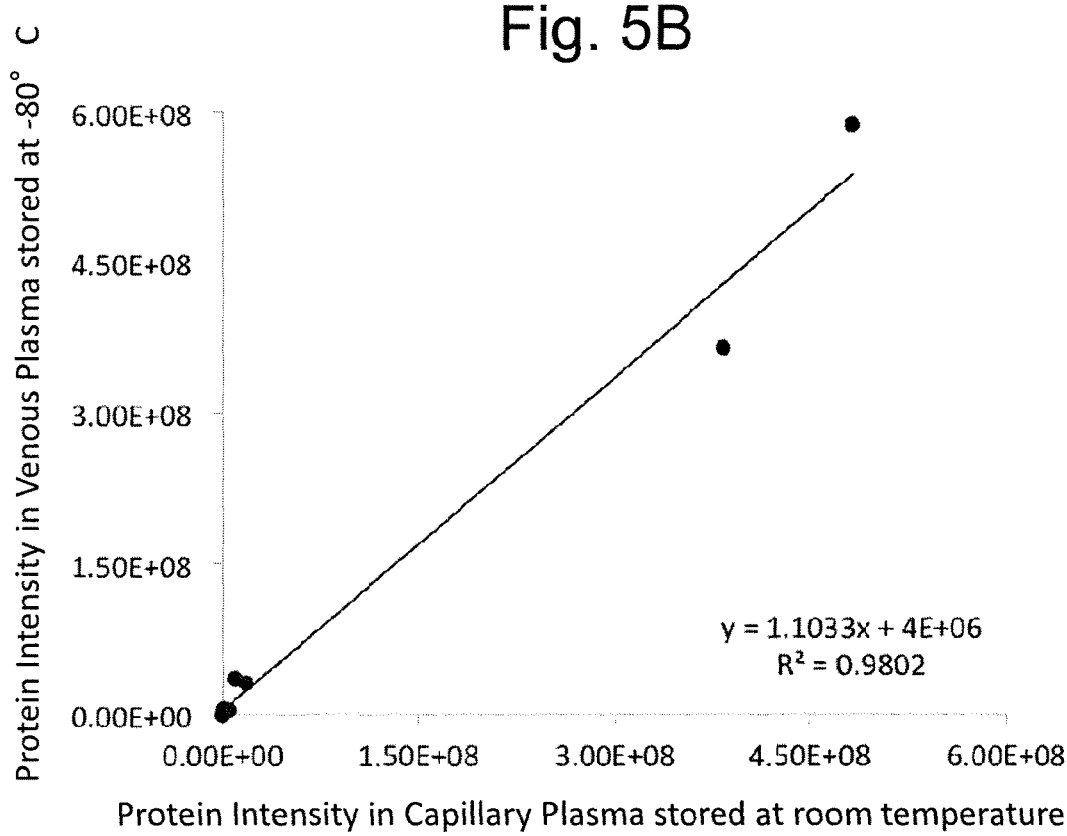

FIG. 5A-5C DIA-type mass spectrometry-derived intensity values for 9 FDA-approved protein biomarkers (each protein is represented by a circle) in a control venous human plasma sample obtained by classical centrifugation of venous blood (10 minutes at 2500 rpm at +4° C.) and stored immediately at −80° C. (y axes) compared to the intensity in capillary human plasma samples (x axes) obtained with a device according to the present invention as shown in FIG. 1 and stored in dry ice (FIG. 5A), +4° C. (FIG. 5B), and at room temperature (FIG. 5C), in each case for 48 hours.

Figure 6A:
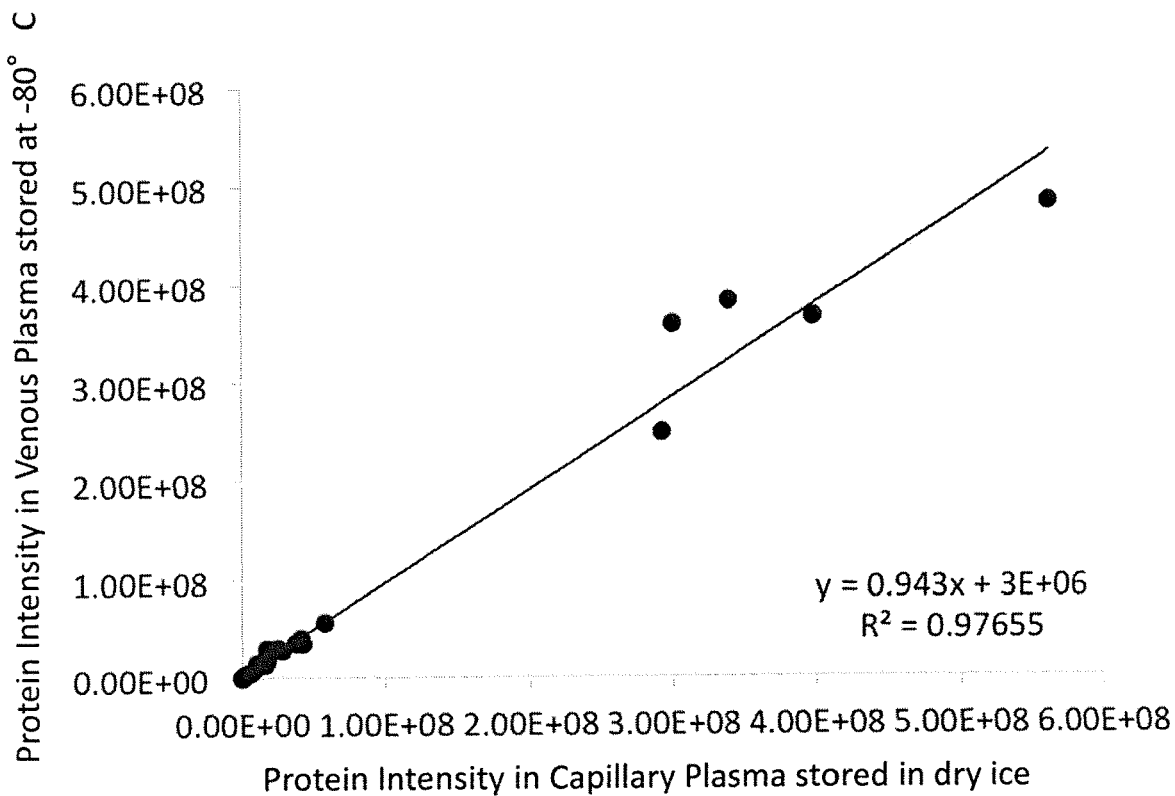
Figure 6B:
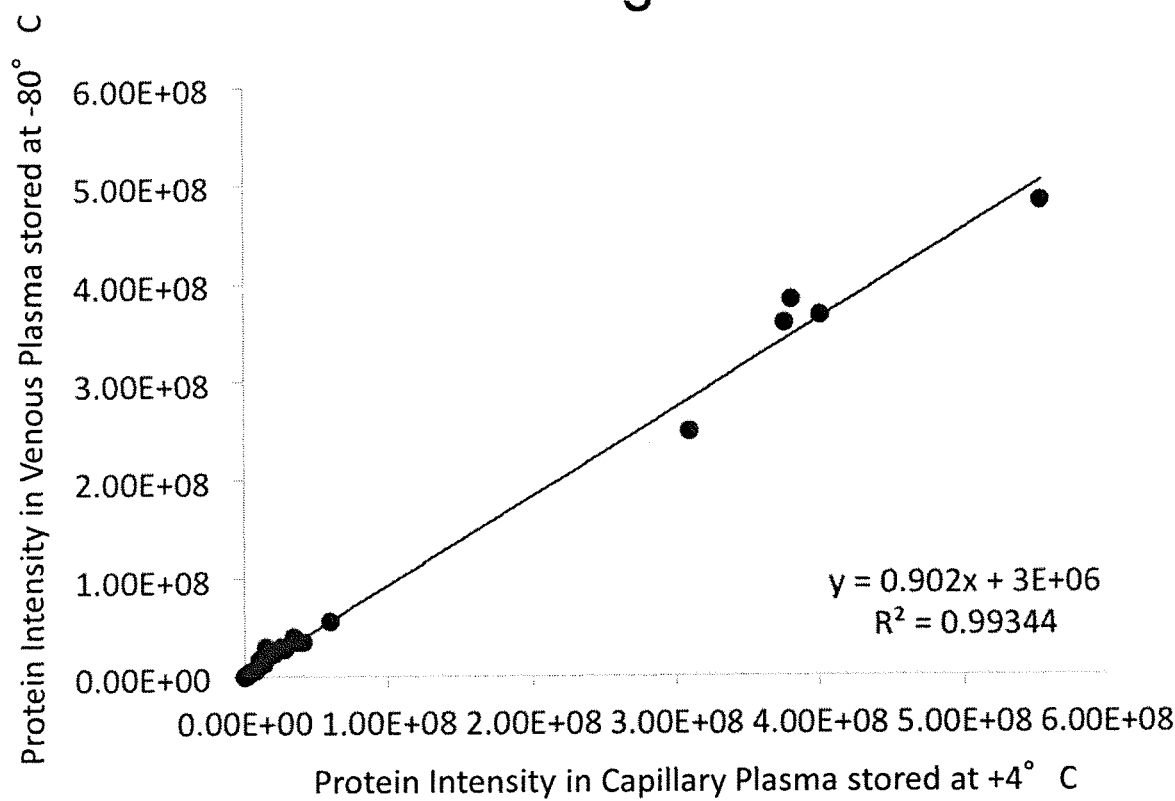
Figure 6C:
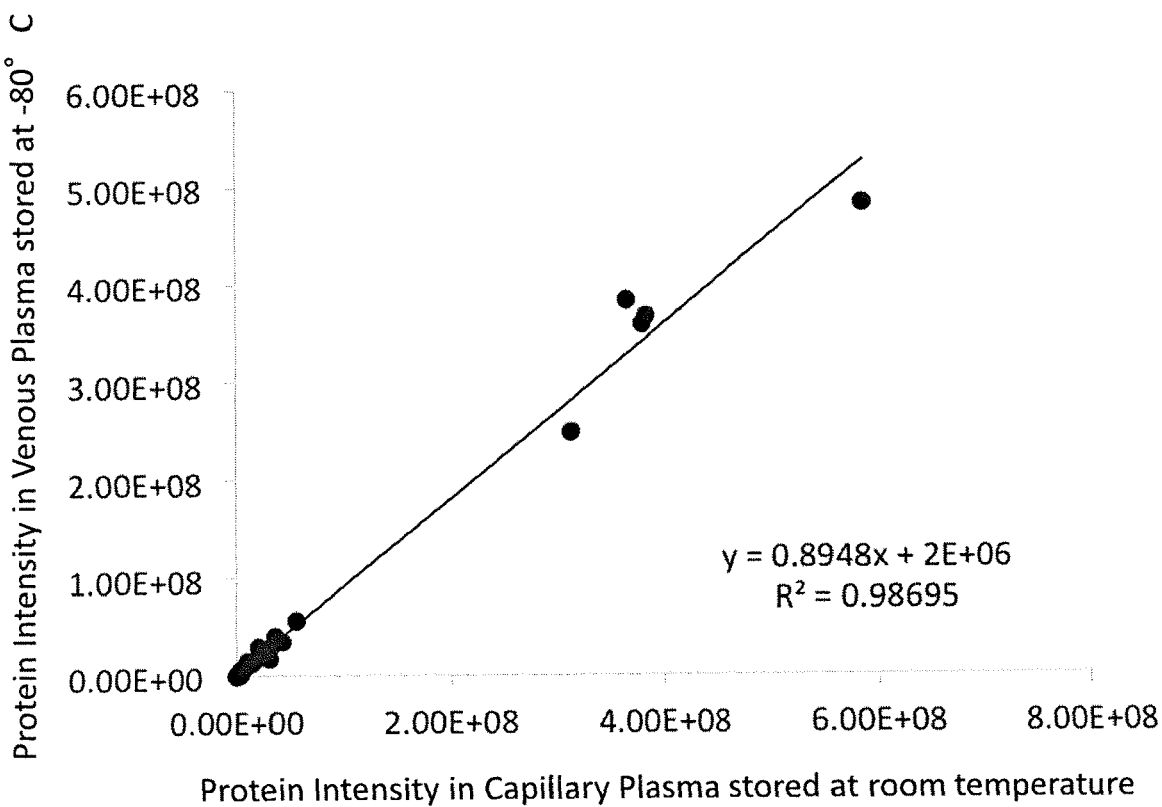

FIG. 6A-6C DIA-type mass spectrometry-derived intensity values for 32 protein biomarkers for ovarian cancer (each protein is represented by a circle) in a control venous human plasma sample obtained by classical centrifugation of venous blood (10 minutes at 2500 rpm at +4° C.) and stored immediately at −80° C. (y axes), compared to the intensity in capillary human plasma samples (x axes) obtained with a device according to the present invention as shown in FIG. 1 and stored in dry ice (FIG. 5A), +4° C. (FIG. 5B) and at room temperature (FIG. 5C), in each case for 48 hours.

Figure 7A:
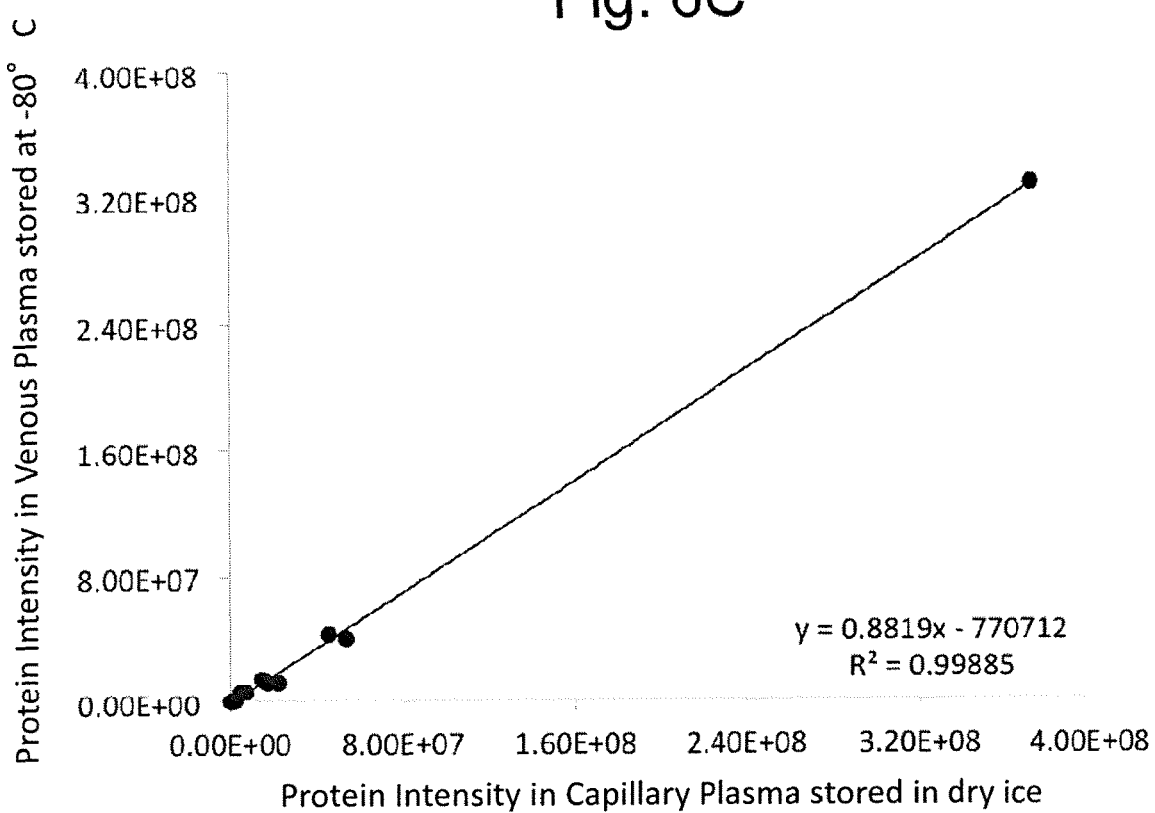
Figure 7B:
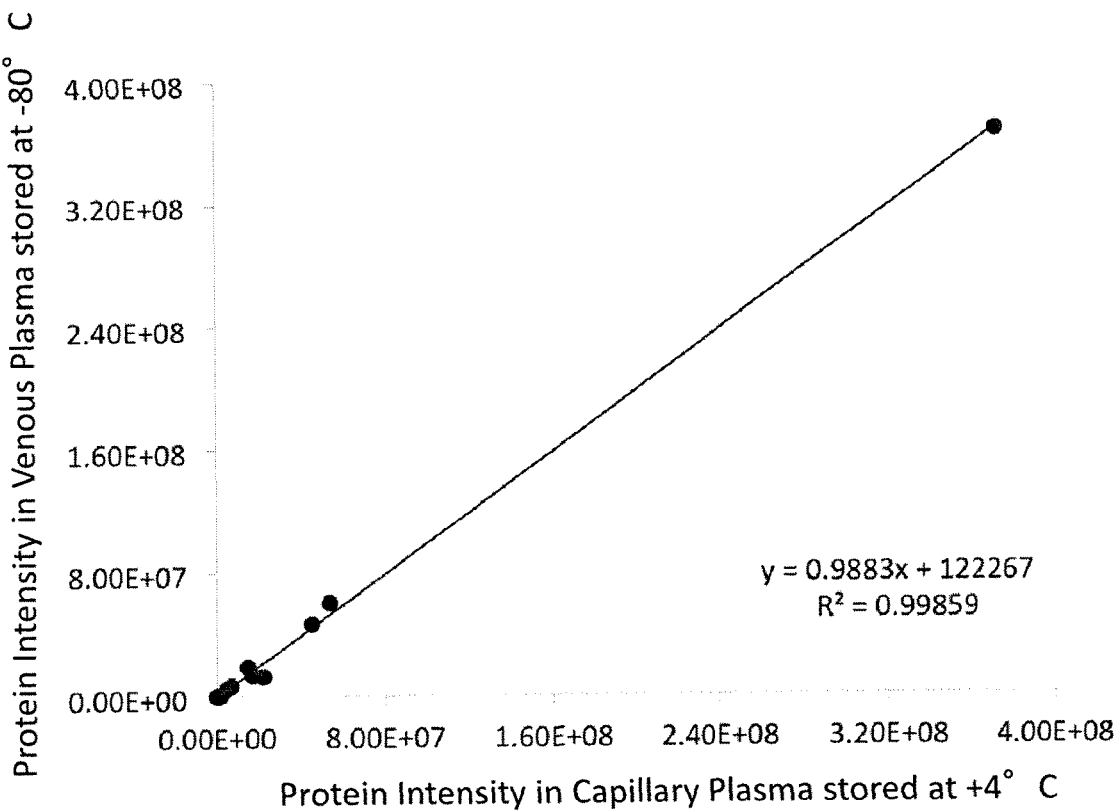
Figure 7C:
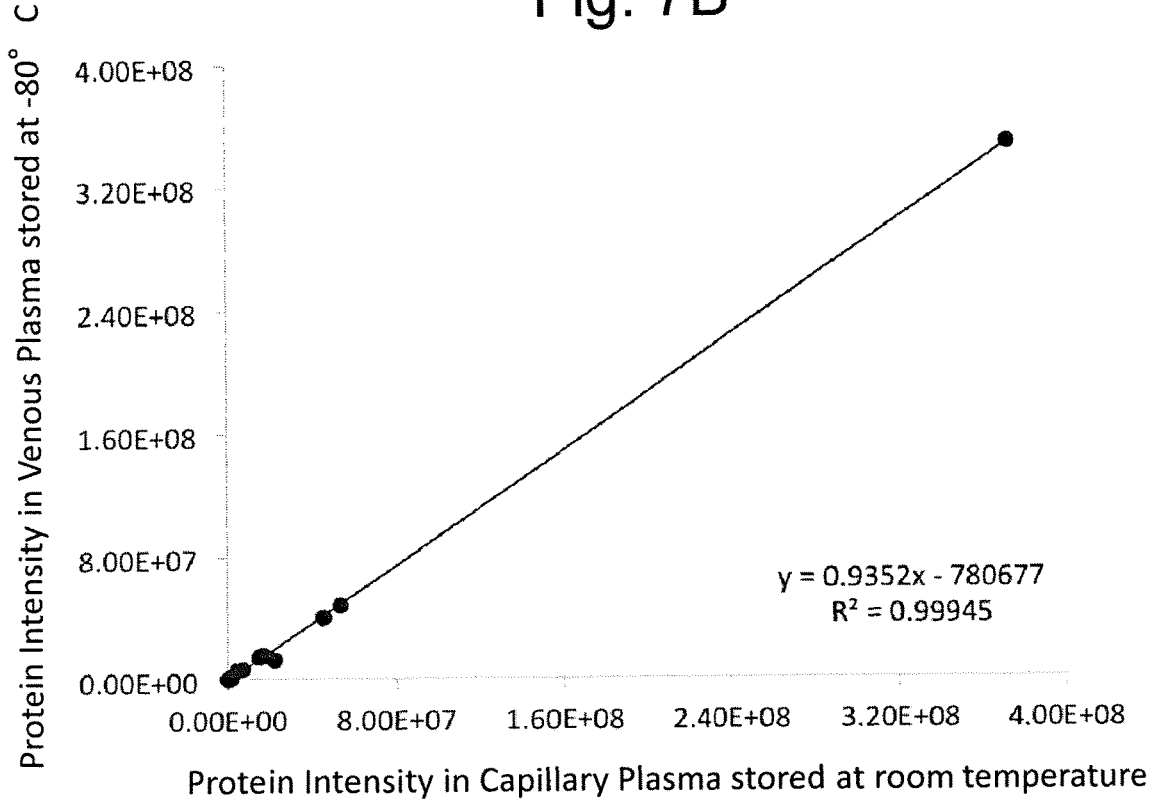

FIG. 7A-7C DIA-type mass spectrometry-derived intensity values for 14 proteins involved in metabolic processes (each protein is represented by a circle) in a control venous human plasma sample obtained by classical centrifugation of venous blood (10 minutes at 2500 rpm at +4° C.) and stored immediately at −80° C. (y axes), compared to the intensity in capillary human plasma samples (x axes) obtained with a device according to the present invention as shown in FIG. 1 and stored in dry ice (FIG. 7A), +4° C. (FIG. 7B) and at room temperature (FIG. 7C), for 48 hours.

Figure 8:
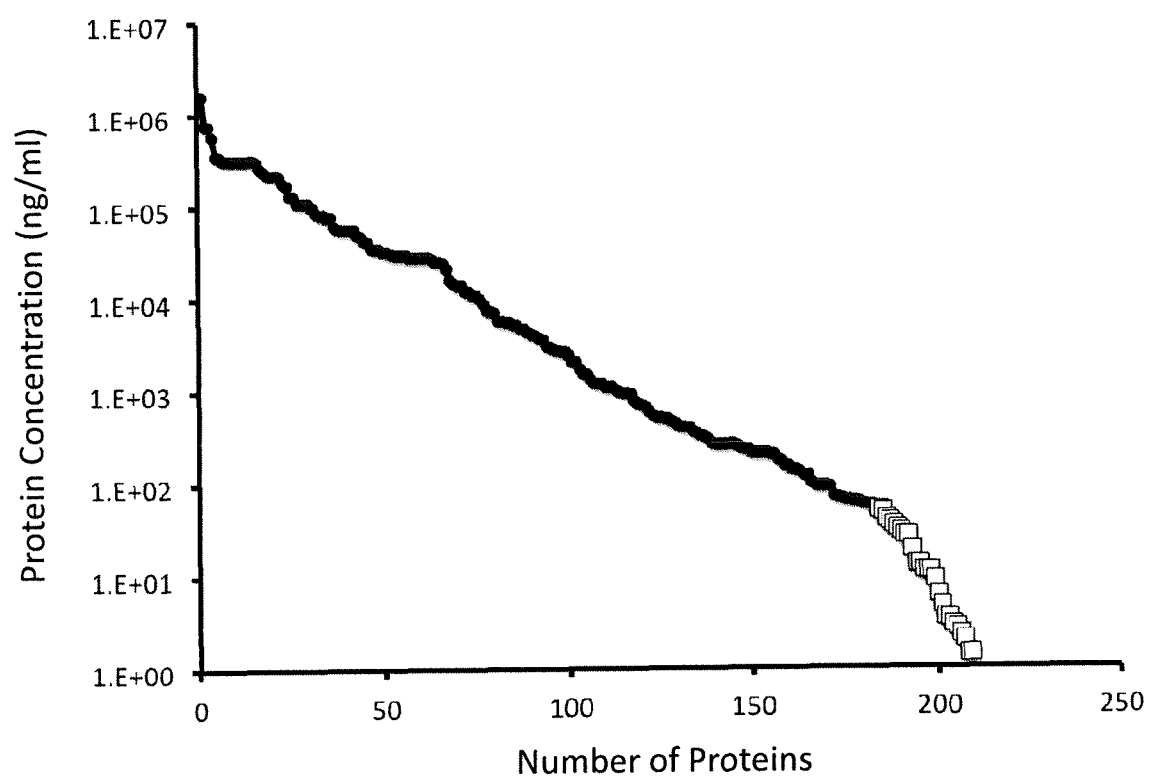

FIG. 8 Dynamic range of protein concentrations for the 511 proteins (filled circles and empty squares) quantified using DIA-type mass spectrometry in a capillary sample stored in dry ice for 48 hours (see Example 4, below). The protein concentrations spanned 6 orders of magnitude with 26 proteins below 50 ng/ml (empty squares). This result indicates that also proteins occurring at a low concentration in blood can be recovered in plasma or serum being separated with the device according to the present invention. Moreover, this result underlines the highly efficient storage/preservation capacities of the device according to the present invention.

FIG. 1A shows a schematic, not to scale illustration of a preferred device 100 for separation of plasma or serum from a blood sample according to the present invention. The device 100 comprises a separation member 20 and an extraction member 30. The device optionally also comprises a sample introduction member 10. Said sample introduction member 10 is preferably configured and positioned relative to the separation member to allow a blood sample 60 to be applied to the separation member 20 via said sample introduction member 10. The device 100 may further comprise a housing. Said housing may comprise or be composed of a housing base 40 and a housing lid 50. The preferred order of assembly of the components of the device 100 is indicated by the arrows in FIG. 1A.

The separation member 20 has a separation member upper surface 23 and a separation member lower surface 24 (the lower surface is not visible in FIG. 1). Preferably, the separation member 20 may have a disk shape. As shown in the detail according to FIG. 1 B the separation member 20 may have a separation member upper portion 21 and a separation member lower portion 22. The separation member upper portion 21 may have pores that allow the liquid components of the blood to pass through and to accumulate at the separation member lower portion 22. The separation member lower portion 22 may have smaller pores that allow serum and plasma to pass through. In other words, the separation member 20 may have pores that gradually decrease in size from the separation member upper portion 21 to the separation member lower portion 22 so that cellular parts of the blood can be trapped in the pores of the separation member upper portion 21. The separation member 20 may be or may comprise a plasma separation membrane or filter known in the art. Said plasma separation membrane/filter preferably uses the filter principle shown in the detail according to FIG. 1B. For example, the separation member 20 may be a Vivid GR membrane, a Cobetter filtration membrane or a Primecare™ membrane. Most preferred is a Vivid GR membrane.

The extraction member 30 of the device 100 according to the present invention has an extraction member upper surface 35 and an extraction member lower surface 36. In an assembled configuration, the extraction member upper surface 35 is in contact, preferably in direct contact, with the separation member lower surface 24. The extraction member 30 is configured to generate capillary forces in order to extract serum or plasma from the separation member 20 (preferably from the separation member lower portion 22). This may be achieved by an extraction member 30 that comprises an extraction member base 31 (preferably being a base plate) and one or more microstructures 32 protruding (preferably substantially perpendicular) from said base 31. The microstructure(s) 32 protruding from said base 31 are preferably micro-pillars. The one or more microstructures 32, preferably the micro-pillars, are preferably integrally formed with the extraction member base 31, i.e. they are made in a single piece.

The extraction member base 31 may be solid, rigid, self-supporting and/or unitary. Preferably it may be a base plate with said properties. The extraction member base 31 or base plate may in particular not be formed from a paper, paper-like or any other water absorbing fibrous material. Similarly, also the one or more microstructures 32 (e.g. micro-pillars) may be solid, rigid and/or self-supporting. Preferably, the one or more microstructures 32 (e.g. micro-pillars) may be rigid, self-supporting and/or unitary. The one or more microstructures may in particular not be formed from a paper, paper-like or any other water absorbing fibrous material. It is preferred that the one or more microstructures 32 are formed from the same material as the extraction member base 31. Accordingly, it is preferred that the extraction member 30 is solid, rigid and self-supporting. These properties of the extraction member 30, its base 31 and/or its microstructures 32 may contribute to the advantage of storing plasma or serum in a liquid form within the extraction member.

The extraction member 30 of the device 100 may be made or formed from plastic, photoresist resin or any polymeric material. For instance, the extraction member 30 may be made (or formed) from polyamide. The extraction member 30 may, for example, be made (or formed) from nylon, polyether ether keton, acrylic or acrylic-derivatives such as poly(methyl methacrylate), Cyclic Olefin Copolymer, or epoxy SU-8. A particularly preferred material is polyamide since this material is already used in several clinical settings. However, the extraction member 30 does not necessarily need to be made or formed from the above-mentioned materials. It may alternatively also only be covered/coated with said material and may have a core formed from a different material. Preferably, only the surfaces getting into contact with the separated plasma or serum are covered/coated with one of the above-mentioned materials. In principle, also only the extraction member base 31 or the one or more microstructures 32 (e.g. micro-pillars) may be made from or coated with one of the above-mentioned materials.

The dimensions of an extraction member 30 may preferably be selected so that the extraction member fits into a centrifugation tube or can be used as a lid thereof. In this regard a disc like shape may be advantageous. Respective dimensions and suitable centrifugation tubes are mentioned elsewhere herein.

The extraction member upper surface 35 is preferably formed by the upper surface of the microstructures 32 (e.g. micro-pillars). The one or more microstructures 32 can have different shapes and/or cross sections (in a top view). For instance, a microstructure 32 (preferably a micro-pillar) may have a substantially rectangular cross section having a length l and width $w_P$. The length l may be of (about) 0.2 mm to (about) 3 mm, preferably (about) 0.5 mm to (about) 2 mm, more preferably (about) 0.8 mm to (about) 1.2 mm and most preferably (about) 1 mm. The width $w_P$ may be of (about) 0.1 mm to (about) 1.5 mm, preferably (about) 0.2 mm to (about) 1 mm, more preferably (about) 0.3 mm to (about) 0.8 mm and most preferably (about) 0.5 mm. Similarly, the microstructures 32 may have a microstructure height h. The height h of the microstructure 32 may be of 0.1 mm to 1 mm, preferably of 0.2 mm to 0.7 mm, even more preferably of 0.3 mm to 0.5 mm and most preferably of 0.3 mm. The preferred heights have been found to be beneficial for increasing the capillary forces generated and/or for increasing the volume of extracted serum or plasma. If more than one microstructure 32 is employed (e.g. a pattern or array of microstructures), all microstructures 32 may have the same shape and/or cross section (e.g. the same dimensions). The height of the microstructures 32 is preferably substantially equal. Further, the upper surface of the microstructures 32 is preferably substantially flat. These two preferred properties are beneficial to bring the extraction member upper surface 35 in direct contact with the separation member lower surface 24.

Figure 1C:
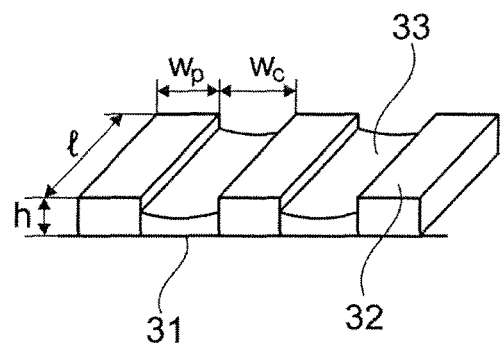

As shown in the detail according to FIG. 1C, the extraction member 30 may comprise one or more channels 33 having a channel opening width or spacing $w_c$, a channel length and a height h. The separated plasma or serum may be collected and/or stored in the channels 33. The one or more channels 33 are preferably formed by the one or more microstructures 32 in conjunction with the extraction member base 31. Accordingly, the channel height is preferably defined by the height h of the microstructures 32. The length of the channels may be defined depending on the shapes of the microstructures 32 defining the same and the pattern in which the one or more microstructures 32 are disposed on the extraction member base 31. In a top view of the extraction member 30, the one or more channels 33 may define a total channel length and the opening width of the channel $w_c$ of said one or more channels 33 at the extraction member upper surface 35 may be at least (about) 1 mm, preferably at least (about) 0.7 mm, and more preferably at least (about) 0.5 mm along at least 50%, at least 60%, at least 70%, at least 80%, or at least 90% of the total channel length.

The extraction member 30 may comprise an organized array of micro-pillars to extract the plasma or serum from the separation member 20 merely by means of capillary forces (and optionally gravity) without the use of external energy sources. The micro-pillar arrays may have different patterns. A respective example is shown in the detail according to FIG. 1C.

The device 100 may further comprise a sample introduction member 10. The sample introduction member may comprise a sample introduction member base 11 that may, for instance, have a disc shape. The sample introduction member 10 may also have sample introduction member rim 12 protruding from the lower surface of the sample introduction member 10, preferably the lower surface of the sample introduction member base 11. Said rim 12 may provide a cavity between the sample introduction member 10 (preferably the lower surface of the sample introduction member base 11) and the separation member 20 (preferably the separation member upper surface 23). Such cavity may be a storage space for blood samples that are applied to device 100 and may prevent spillover when applying a blood sample. The sample introduction member 10 may further comprise one or more through holes 13. The one or more through holes 13 may have different shapes in a top view, but preferably are substantially circular. The opening width or diameter of said through holes 13 may be selected in a manner that blood drops 60, preferably capillary blood drops, can easily pass through the through hole(s) 13. The position of the one or more through holes 13 in the sample introduction member 10 is preferably selected so that the one or more through holes are positioned over the separation member upper surface 23. For instance, the one or more through holes 13 may be provided in a portion of the sample introduction member base 11 that is enclosed by the sample introduction member rim 12.

The separation member 20 preferably is attached, glued, or connected to the sample introduction member 10 only at the outer diameter of the separation member upper surface 23. In particular, the outer diameter of the separation member upper surface 23 may be attached, glued, or connected with the sample introduction member rim 12. With this respect, the width and/or diameter of the separation member may be larger than the width and/or diameter of the rim 12.

The housing base 40 may comprise a housing base plate 41 and/or a housing base plate rim 42 protruding from the upper surface of said housing base plate 41 so as to create a housing base plate cavity 43. The height and/or diameter of the housing base plate cavity 43 defined by the rim may be selected so that it can fit at least the extraction member 30. More preferably, said dimensions may be selected so that the housing base 40 can also fit the separation member 20 and/or the sample introduction member 10. The housing may further comprise a housing lid 50. The housing lid 50 may be configured so as to fit the housing base 40 and to create a cavity in which at least the extraction member 30, but preferably also the separation member 20 and/or the sample introduction member 10, can be stored. Preferably, the housing lid 50 and the housing base 40 can be temporarily attached to each other, e.g. by a screwing mechanism. In other words, the housing lid 50 and the housing base 40 fit each other. Preferably, the cavity formed between the housing lid 50 and the housing base 40 in a closed configuration of the housing may be liquid and/or air-tight. This may protect serum or plasma after separation, e.g. from contaminations. The housing lid 50 may comprise a housing lid base plate 51 and a housing lid rim 52 protruding from the lower surface of the housing lid base plate 51. The dimensions of the housing lid rim 52 may be selected to fit the housing base rim 42. Optionally, the housing lid 50 may comprise a desiccant pellet such as a TBM33® (Wisepac) desiccant pellet. Said desiccant pellet may be permanently or detachably attached to the lower surface of the housing lid 50, preferably the lower surface of the part of the housing lid base plate 51 that is surrounded by the housing lid rim 52. In other words, the desiccant pellet may be placed in the housing lid cavity 53.

Optionally, the housing lid 50 may be configured to act as a manual pump and/or piston. Such manual pump and/or piston may be configured to be manually actuated by the user in order to increase the pressure above the separation member upper surface 23 and/or the differential pressure across the separation member 20. Without wanting to be bound by theory, it is believed that increasing the pressure in this manner may accelerate the separation of blood components in the separation member 20 and/or increase the plasma yield. For this purpose, the housing lid 52 may be slidable with respect to the housing base 40. In particular, the housing lid 52 may be slidable onto and/or into the housing base 40. In the assembled state of the device 100, the housing lid 52 may be configured to be pushed towards the housing base 40 to compress the air above the separation member 20. The space below the separation member 20 may be vented, e.g. by providing a vent in the housing base 40. For example, the housing lid rim 52 may be configured to be a close fit with the housing base plate rim 42. The fit may be substantially or entirely airtight. Alternatively or additionally, the housing lid 50 may be provided with one or more projections (not shown) that protrude into the through holes 13 in the sample introduction member 10. The projections may seal with the through holes 13 so that the air in the sample introduction member 10 is compressed when the housing lid 50 is pushed with the projections towards the sample introduction member 10 and/or towards the housing base 40.

Figure 1D:
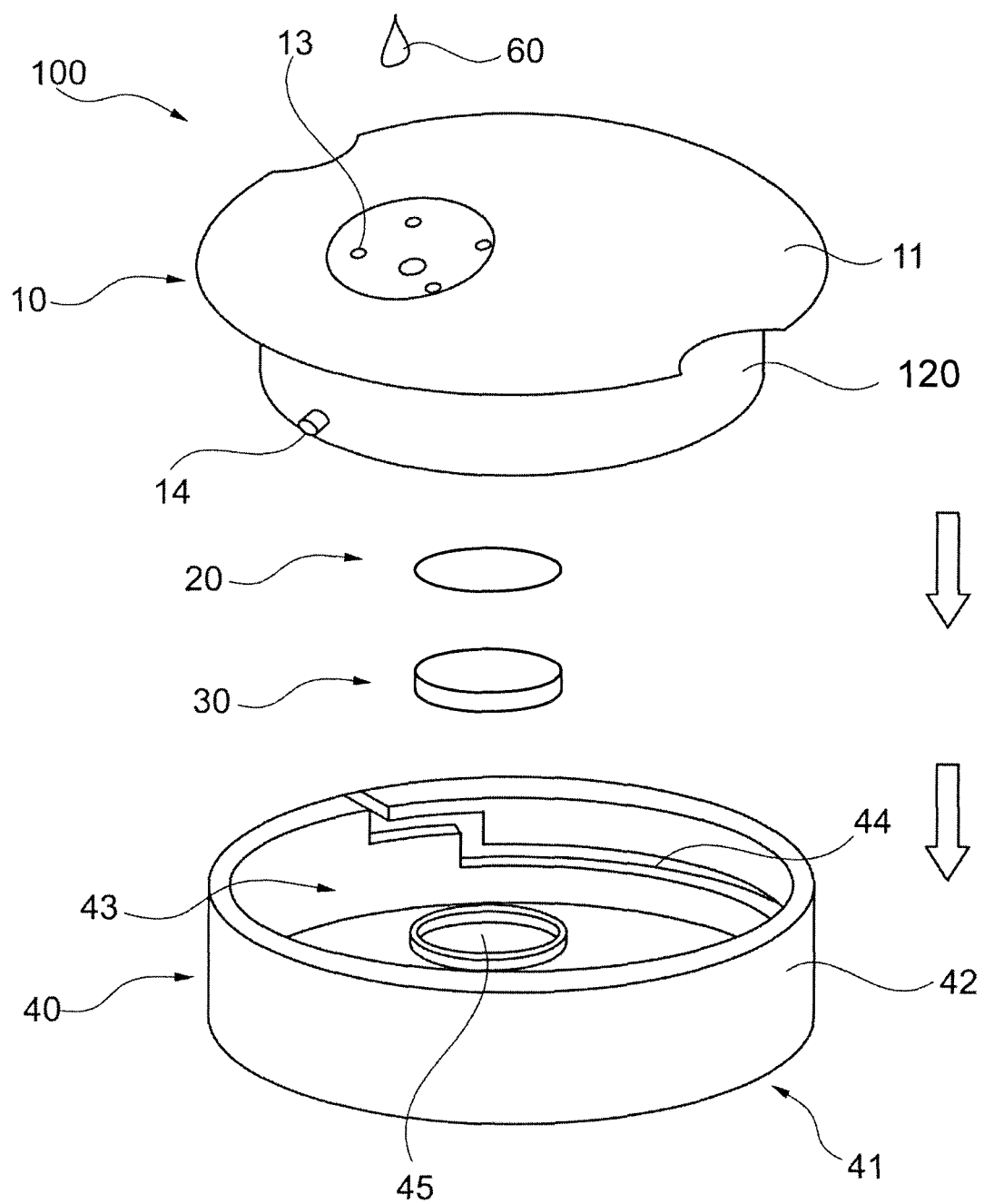
Figure 1E:
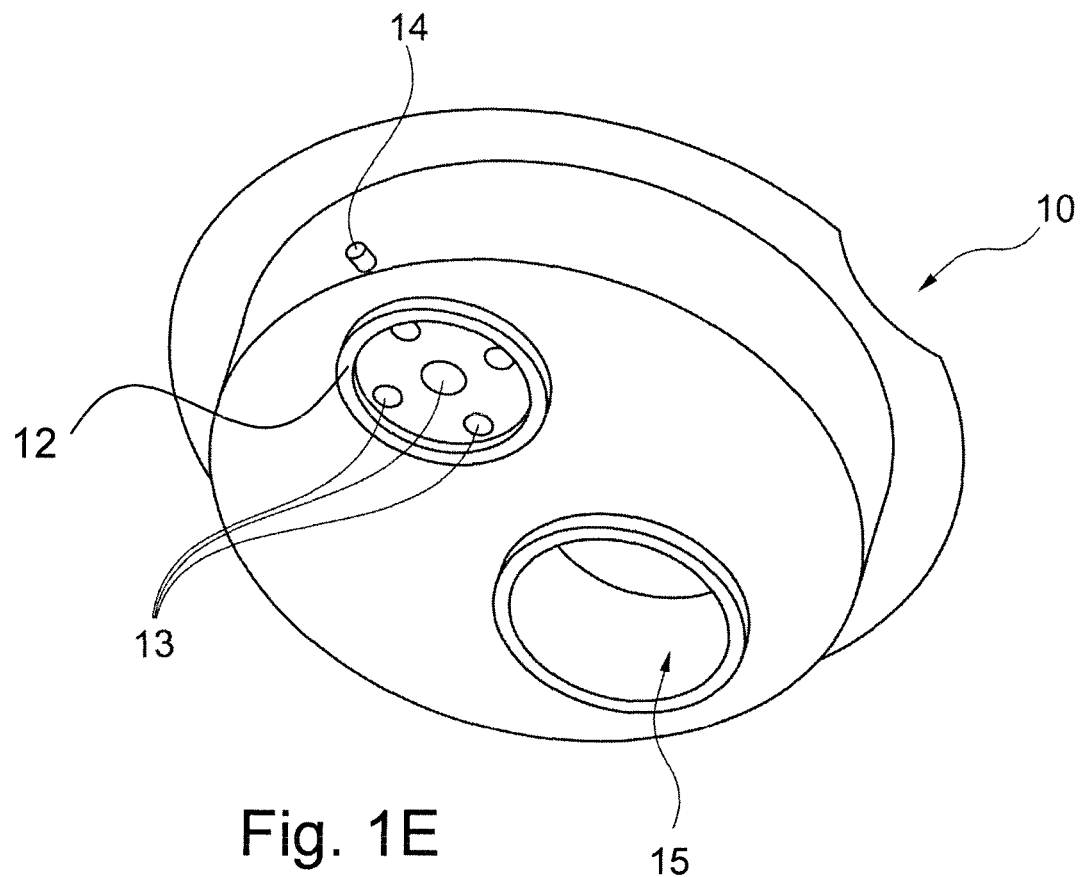
Figure 1F:
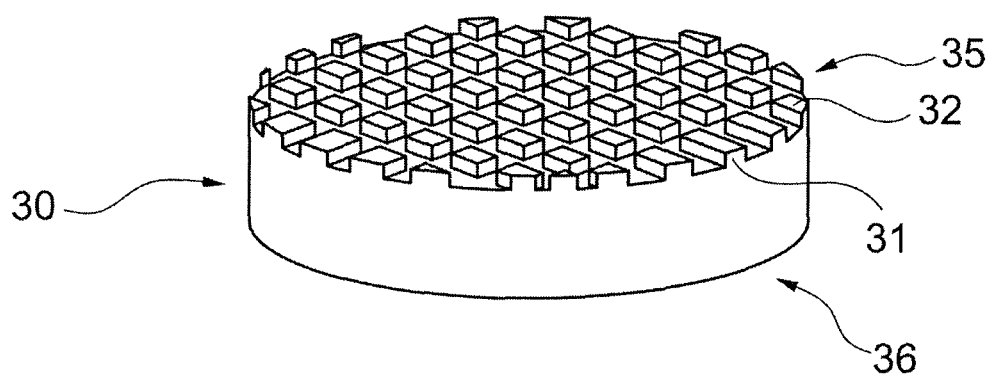

FIGS. 1D to 1F show a device 100 according to the present invention or parts thereof in more detail. Corresponding elements are denominated with the same reference numerals. The description provided above equally applies to this further device and its elements and the explanations below thus focus on additional (optional) features shown in FIGS. 1D, 1E and 1F.

As shown, also the device 100 comprises a separation member 20 and an extraction member 30. Also in this case, a sample introduction member 10 to allow a blood sample 60 to be applied to the separation member 20 and a housing base 40, in which the separation member 20 and/or the extraction member 30 may be received, may be provided. The device 100 of FIGS. 1D to 1F may also comprise a housing lid (not shown in these drawings), as explained above.

As shown in FIGS. 1D and 1E, the sample introduction member 10 may be provided with one or more through holes 13, for example 2 or more, or 3 or more through holes 13 (e.g., five). The through holes are preferably positioned above the cavity provided by the sample introduction member rim 12, which cavity preferably is arranged between the lower surface of sample introduction member base 11 and the upper surface of the separation member 20. This positioning of the through hole(s) allows the blood to enter said cavity. Optionally, the through holes 13 may be arranged in a recess in which the blood sample 60 may be gathered before it flows into the separation member 20.

Figure 1G:
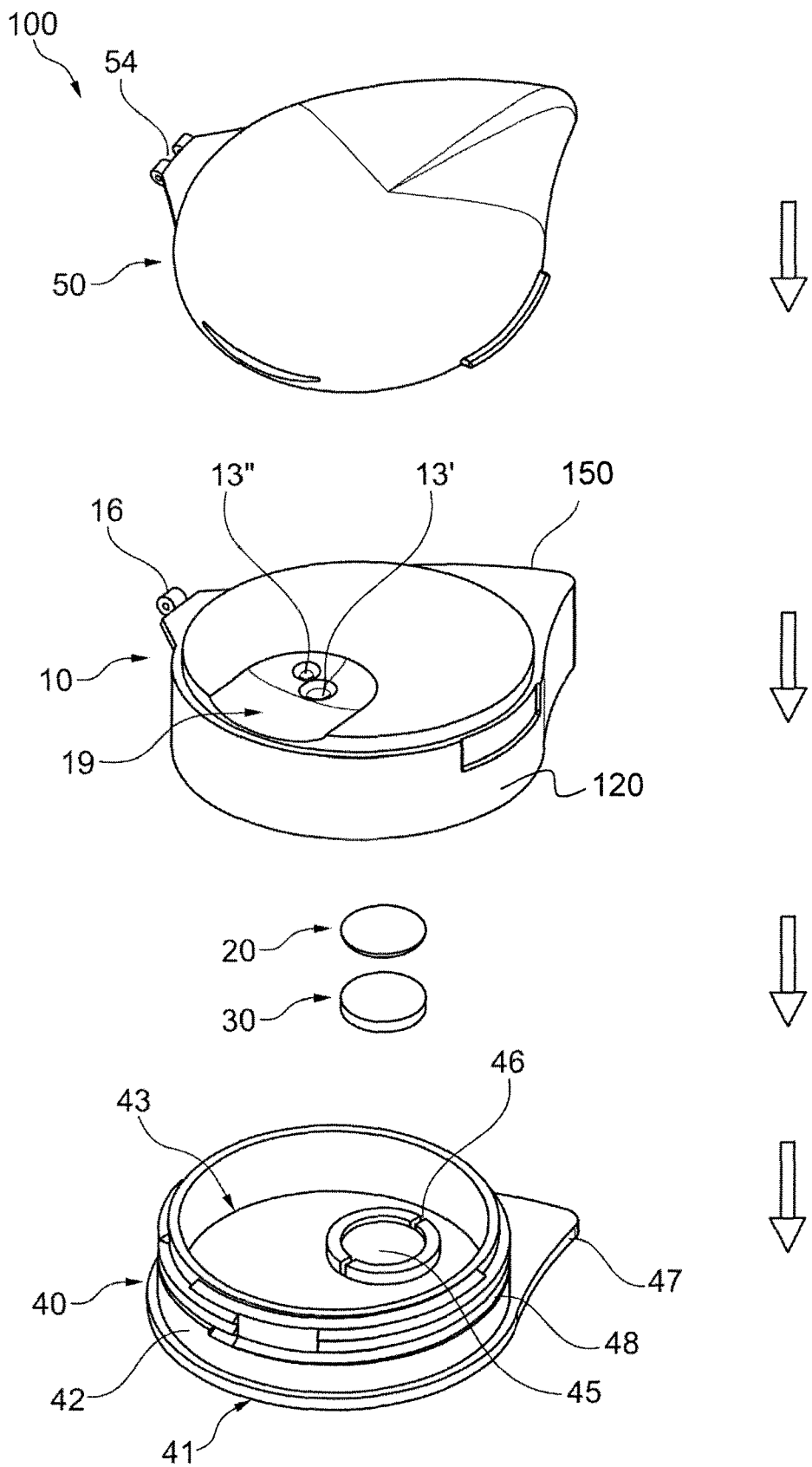
Figure 1H:
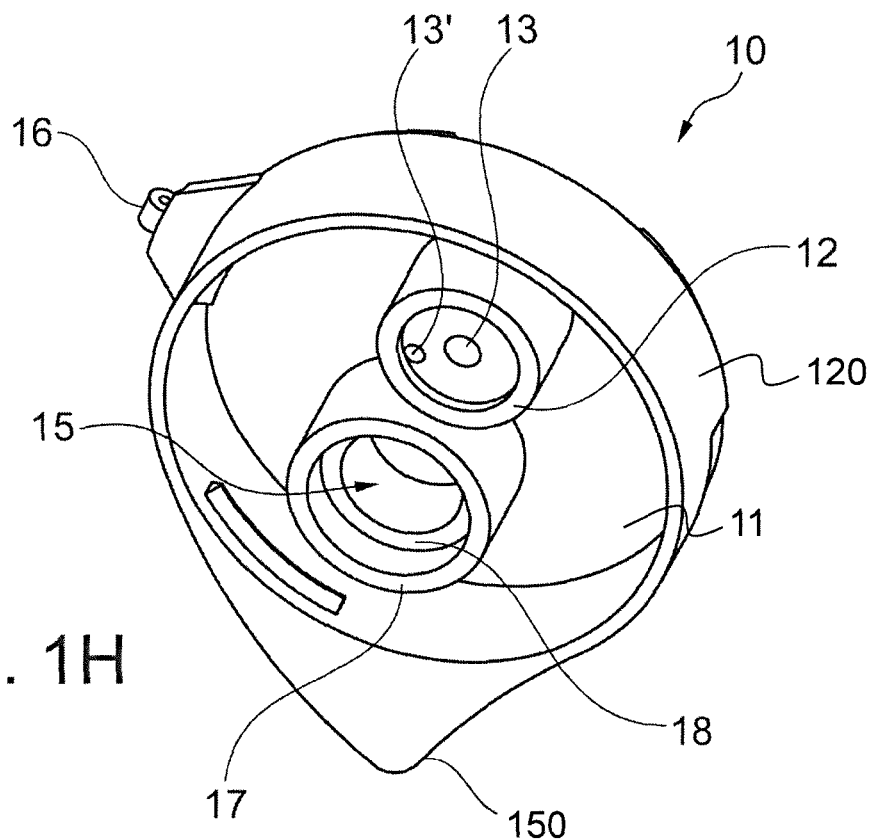
Figure 1I:
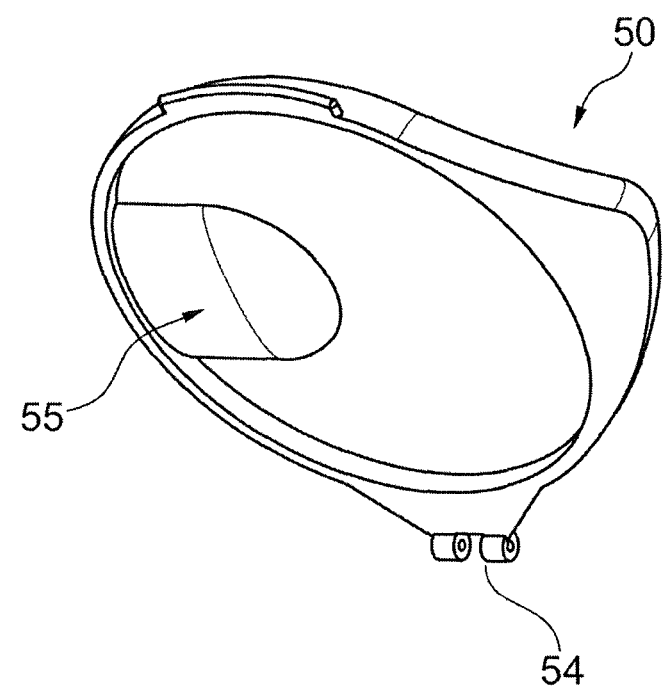

As described above, a device 100 according to the present invention may also comprise a housing lid 50 (not shown in FIGS. 1D and 1E, but see FIGS. 1G and 1I). The housing lid 50 may be configured to seal the sample introduction member 10 (in particular, the holes 13), preferably in an air-tight manner. For example, the lower surface of the housing lid 50 may match the upper surface of the sample introduction member 10. The lower surface of the housing lid 50 may have a protrusion 55 that fits (preferably exactly fits) into a recess 19 on the upper surface of the sample introduction member 10 in which the blood sample may be gathered before it flows through the holes 13 on the separation member 20.

The through holes 13 may have similar shapes and/or dimensions (e.g. diameters). Alternatively the through holes may have different dimensions (see FIGS. 1G and 1H). For instance, one or more first through holes 13' and one or more second through holes 13" may be provided, wherein the second through holes have smaller dimensions (e.g. a smaller diameter) than the first through holes. The larger first through hole(s) 13' may be configured for introduction of the blood sample 60. The second through hole(s) 13" may be configured to act as ventilation openings, i.e. may be used for air exchange. Such ventilation openings may release air that is displaced by introduced blood and may thereby prevent that pressure builds up in the cavity between the sample introduction member 10 (preferably the lower surface of the sample introduction member base 11) and the separation member 20 (preferably the separation member upper surface). In other words, the second openings may help to release air when blood is introduced via the first opening(s) 13', i.e. may prevent that pressure is built up, e.g. in the cavity in which the blood sample 60 may be gathered before it flows into the separation member 20.

As shown in FIG. 1E, the sample introduction member 10 may further comprise a recess 15 in which a desiccant (e.g. a desiccant pellet such as a TBM33® (Wisepac) desiccant pellet) may be received. The recess 15 may be provided in a surface of the sample introduction member 10 that faces the separation member 20 and/or the extraction member 30 when the device 100 is assembled. The recess 15 may be formed by a rim protruding from the lower surface of the sample introduction member 10 (see FIG. 1H). Said rim may be a step-like rim. For instance, the rim may be formed by an outer rim 17 protruding from the lower surface of the sample introduction member 10 that faces towards the separation member 20 in an assembled configuration of the device (see FIG. 1E) and an inner rim 18 which protrudes less from the lower surface of the sample introduction member 10 that faces towards the separation member 20 in an assembled configuration than the outer rim 17 and has a smaller diameter than the outer rim 17. Preferably, the outer rim 17 and the inner rim 18 are integral to form a step-like rim structure without any gap being formed between the outer rim 17 and the inner rim 18. A desiccant (e.g. a desiccant pellet such as a TBM33® (Wisepac) desiccant pellet; not shown in the figures) may be placed in the part of the volume of the recess 15 defined by the inner rim 18. A protection membrane (not shown in the Figures) may be placed on top of the desiccant (e.g. may be glued on the face of the inner rim 18 facing the housing base 40) and/or such that the protection membrane may be interposed between the desiccant and the extraction member 30. Preferably, the protection membrane allows air exchange. For instance, the protection membrane may be a filter or a filter paper.

Accordingly, the recess 15 may be a desiccant chamber. Said desiccant chamber may be formed by two rims of different diameter and height, the inner rim 18 having a lower height than the outer rim 17. Preferably the recess defined by the inner rim 18 is filled with desiccant and is covered with a protection membrane that allows air-exchange, such as a filter paper.

In order to hold the components of the device 100 together in the assembled state, the sample introduction member 10 and/or the housing lid (not shown in FIGS. 1D and 1E, but see FIGS. 1G and 1I) may comprise a locking arrangement for engaging with the housing base 40. The locking arrangement may be provided by, for example, a snap-fit, a bayonet connection, and/or a corresponding tongue and groove arrangement. For example, as shown in FIGS. 1D and 1E, the sample introduction member 10 may be provided with a pin 14 that engages with an internal groove 44 in the housing base 40. As will be evident to the skilled person, the groove 44 could also be an external groove. Moreover, several grooves and/or pins could be provided. As shown in FIG. 1G, the groove could also be a threading, e.g. on the sample introduction member 10 and the housing base 40. A threading may, for instance be provided on the outer surface of the housing base plate rim 42. A corresponding threading may be provided on an inner side of a rim 120 extending from the sample introduction member base 11 (see FIG. 1H). This arrangement could also be inversed.

As further shown in FIG. 1D, the housing base 40 may be provided with a rotation stop feature 45. The rotation stop feature 45 may be configured to cooperate and/or engage with a corresponding rotation stop feature (not shown) provided on the extraction member 30 to inhibit rotation of the extraction member 30 in the housing base 40. The rotation stop feature 45 may be provided by one or more protrusions and/or one or more recesses in the cavity 43 of the housing base 40, e.g. one or more protrusions and/or one or more recesses on the base and/or on the sidewalls of the cavity 43.

The rotation stop feature 45 may be formed by a rim-like protrusion on the base of the cavity 43. The rim-like protrusion may be continuous or discontinous. For instance, the rim-like protrusion may comprise one or more (e.g. at least two or at least three) notches or slits 46. Such notches or slits may be configured to allow introducing a thin pointy object, e.g., in order to facilitate removal of the extraction member 30 after serum or plasma has been collected in the extraction member 30.

FIG. 1G shows a device 100 according to the present invention. FIGS. 1H and 1I show certain parts thereof in more detail. Corresponding elements are denominated with the same reference numerals as used above. The description provided above equally applies to this further device and its elements and the explanations below thus focus on additional (optional) features shown in FIGS. 1G, 1H and 1I, as far as not already discussed, above.

As illustrated in FIG. 1G the device 100 may comprise a lid 50. Said lid 50 may be connectable to the sample introduction member 10 via a hinge 54, 16, which may be connected by a tighter metal cylinder (not shown). The lid 50 may be configured to close the device 100 in an air-tight manner. For instance, its lower surface may match the upper surface of the sample introduction member 10.

The different parts of the device 100, e.g. as shown in FIG. 1G may be connected to provide a fully closed configuration (e.g., an air-tight configuration) to reduce the risk of contamination of the extraction member 30.

The device 100 according to the present invention may comprise a sample introduction member 10 that is connected to the housing base 40. For instance, the connection may be achieved via a threading or a bayonette connection. Preferably, as shown in FIG. 1G the connection allows the sample introduction member 10 and the housing base 40 to be rotatable against each other along the longitudinal axes of the device and/or both parts. The sample introduction member 10 and the housing base 40 may be rotatable against each other over a certain predefined maximum angle. The sample introduction member rim 12 protruding from the lower surface of the sample introduction member base 11 may be arranged at a first position, said first position being preferably directly above the extraction member 30. The diameter of the rim 12 may correspond to the diameter of the extraction member 30 to achieve a complete overlap. The rim(s) forming the recess 15 (e.g. the outer rim 17) may be arranged at a second position. Said second position is preferably arranged relative to the first position such that rotation of the sample introduction member 10 against the housing base 40 (or vice versa) over the predefined angle results in the recess 15 being positioned over the extraction member 30, preferably overlapping the extraction member 30 completely (i.e. at the position the sample introduction member rim 12 was before rotation). Preferably also the rim forming the recess 15 (e.g. the inner diameter of the outer rim 17) may have the same diameter as the extraction member 30. The predefined angle of rotation may be 180° C.

Accordingly, the device 100 may have two configurations, between which a user can change by rotating the sample introduction member 10 and the housing base 40 against each other for a predefined angle. In the first configuration (referred to as "open drop position"), which is preferably the predefined configuration of the assembled device, the sample introduction member rim 12 is positioned above the extraction member 30. Preferably, the lower surface of the separation member 20, which may be fixed to the sample introduction member rim 12 as described elsewhere herein, is in contact with the upper surface of the extraction member 30, preferably in intimate contact. The extraction member 30 is preferably held in a defined position in the housing base 40. In the "open drop position" a blood sample 60 may be introduced and separated plasma or serum may be gained and collected in the extraction member 30. In the second configuration (referred to as "close drop position"), which differs in that the sample introduction member 10 is rotated against the housing base 40 (or vice versa) for a predefined angle, the recess 15 is positioned above extraction member 30. The "close drop position" allows that a desiccant placed in recess 15 or a part volume thereof (e.g. formed by an inner rim 18) is positioned directly above the extraction member. Thereby drying of separated plasma or serum can be facilitated. Preferably the rotation stop feature 45 may and the rim forming recess 15 may engage in a air tight manner to additionally facilitate drying of the serum by creating a closed volume comprising the extraction member 30. Due to the closed volume being relatively small, humidity can be reduced more efficiently by the desiccant. Preferably, a filter (e.g. a filter paper) may protect the desiccant from getting into direct contact with the extraction member 30 or the serum/plasma stored in the extraction member 30.

To ensure that changing between the "open drop position" and the "close drop position" can be achieved accurately, the device 100 may comprise one or more position indicators that mark the rotation position of the sample introduction member 10 and the housing base 40 against each other in which the device is in the "open drop position" and/or the "close drop position". A person skilled in the art will appreciate that different types of position indicators may be provided. Non-limiting examples are markers/labels on respective positions of the sample introduction member 10 and/or the housing base 40. For instance a first protrusion 150 may be provided on the sample introduction member 10 and a second protrusion 47 may be provided on the housing base 40 (see FIG. 1G). When both protrusions are aligned this may indicate that the device 100 is in the "open drop position" or the "close drop position". This will depend on the positioning of recess 15 and the sample introduction member rim 12 on the lower surface of the sample introduction member 10, which faces the housing base 40. In the exemplary configuration shown in FIGS. 1G and 1H, alignment of the protrusions indicates the "close drop position" which facilitates drying of the separated serum or plasma. The first and/or second protrusion may extend radially, e.g. radially from the sample introduction member 120 and/or the housing base 40, respectively.

The mechanism allowing rotation between the sample introduction member 10 and the housing base 40 against each other along their longitudinal axis (e.g. threading) may be configured to be secured, i.e. that rotation is only possible if a security mechanism is overcome. For instance, a threading may be configured in a manner that the two parts need to be pressed against each other before rotation is possible. Such a mechanism may prevent that the position of the device, which may be delivered in a ready-to-use setting, i.e. in a "open drop position" may be accidentally manipulated by the user before usage. In particular, this may prevent that the extraction member 30 is not perfectly positioned below the separation member 20 and the sample introduction member rim 12.

As shown in FIGS. 1G and 1I, the device 100 may comprise a housing lid 50. The housing lid 50 may be connected (detachably or not) to the sample introduction member 10, e.g. to its upper surface or its side wall. The connection may be provided by a hinge 16, 54 that allows the lid to be opened and closed without removing it from the device 100 (see FIGS. 1G to 1I). In principle, the lid 50 may also be connected with the housing base 40 and the sample introduction member 10 may be placed as a separate part between the housing base 40 and the housing lid 50. Also in this context a hinge may be used as connection.

The housing lid 50 may be configured to close the device air-tightly. Preferably, the housing lid 50 may be configured to close all through hole(s) 13 or only some of them, such as the first through hole(s) 13', air tightly. The housing lid 50 may, for instance, comprise a housing lid protrusion 55 on its lower surface which matches the recess 19 on the upper surface of the sample introduction member 10. Optionally, the device 100 may be configured so that the housing lid 50 can be closed during the process of separation into plasma or serum. Such a configuration has the advantage that the risk of sample contamination is further reduced.

The device 100 as exemplified in any one of the FIGS. 1A to 1I above may be employed with any extraction member 30 as described herein elsewhere.

The present invention is additionally illustrated by way of the following examples that provide a better understanding of the present invention and of its advantages.

Example 1: Optimization of Extraction Performance

In the present Example two different configurations of the extraction member of a device according to the present invention (specifically having the components as shown in FIG. 1A) were compared as regards their extraction performance. The devices were identical except for the extraction member used.

The two devices employed the plasma separator membrane Vivid GR as a separation member. The Vivid GR membrane traps the blood cells and allows the passage of the liquid phase (plasma/serum) to the bottom of the membrane (see FIG. 1B). However, the plasma does not substantially flow out of the membrane passively. To extract the plasma from the separation membrane lower surface, an extraction member was employed in both devices tested. The extraction member contacted the lower surface of the separation membrane and extracted the plasma into the extraction member. Both devices tested comprised a polyamide (PA) plastic disc (1 cm of diameter) as an extraction member. With the aim of extracting and also storing the plasma/serum inside the extraction member, the upper surface of both PA discs was machined in order to create an extraction member having a base and microstructures protruding upward therefrom and empty spaces between said microstructures. The two different devices employed in the context of the present invention differ in the patterns on the extraction member upper surface. The extraction member of the first device had micro-pillars extending over the whole disk diameter (also referred to as "lines"); the second device had shorter micro-pillars each having a length of 1 mm and with a space of 0.5 mm being provided between adjacent micro-pillars in the lengthwise direction. In both cases the micro-pillars had a width $w_P$ of 0.5 mm and a height 0.5 mm. The open width $w_c$ of the channels was 0.5 mm.

For the experiments characterizing the extraction performance, the respective parts of the two devices were first assembled in accordance with the scheme shown in FIG. 1A (following the arrows in FIG. 1A). Next, the following steps were performed for plasma separation from mouse blood samples:

First, 110 µl of mouse blood were directly applied (dropwise) to the sample introduction member of said devices. After 10 minutes in vertical position (in the orientation as shown in FIG. 1) at room temperature, both the sample introduction member and the attached plasma separation membrane were removed from the extraction. The lid was used to close the device, storing the plasma extraction element inside. Finally, the volume of the extracted plasma was measured by centrifugation of the extraction disc into an eppendorf tube followed by weighting the tube filled with plasma in a precision scale (a calibration curve was previously constructed with plasma volumes ranging from 5 to 50 microliters).

As shown in FIG. 2A (first two bars on the left), the amount of plasma collected is similar when using both patterns. This illustrates that different microstructures and micro-pillar dimensions may be employed in the context of the extraction member of a device according to the present invention. However, due to larger overall storage capacity of the micro-pillar pattern, the micro-pillar pattern is believed to be advantageous over the "linear" pattern. Moreover, the large overall storage capacity of the micro-pillar pattern also may be advantageous when preloading the extraction member with different solutions. Due to the advantages of an extraction member comprising discontinued micro-pillars, the devices used in the following experiments described herein included this configuration of the extraction member.

Next, further experiments to assess preferable micro-pillar heights h and the spacing between micropillars $w_c$, respectively were performed. In other words, it was assessed with which micro-pillar height h and spacing $w_c$ between adjacent micropillars most plasma could be extracted from the separation member. To this end, the volume of plasma extracted by a disc-shaped plasma extraction elements of 1 cm of diameter with discontinued micro-pillars of different heights and different spacings $w_c$ between micropillars was measured, respectively (otherwise the device was the same as used above and as shown in FIG. 1). As shown in FIG. 2 FIGS. 2A and 2B, respectively, 0.3 mm was determined to be the preferable height and 0.5 mm the preferable spacing since the maximum volume of plasma could be extracted.

Without intending to be bound by theory, the micro-pillar dimensions selected for the subsequent experiments/examples and believed to be optimal for recovering as much serum or plasma as possible were 0.3, 0.5 and 1 mm (height h, width $w_P$ and length l, respectively). The spacing we between the micro-pillars was selected as 0.5 mm in the following Examples.

Example 2: Separation of Plasma from Human Capillary Blood

In this example, the performance of a device with the above-mentioned preferred dimensions in a real direct-to-costumer scenario was assessed. A volunteer followed the recommended WHO guidelines for capillary blood sampling by using a fingerprick (see WHO Guidelines on Drawing Blood: Best Practices in Phlebotomy (Geneva; 2010)). Next, the volunteer applied 8 or 10 capillary blood drops into the through holes of the sample introduction member. After 10 minutes at room temperature and with the device in vertical position, the plasma collected in the extraction member was measured. As shown in FIG. 2C, >10 µl of human plasma were reproducibly obtained with both volumes of blood (n>5 individual samplings). Therefore, these data clearly demonstrate the feasibility of obtaining meaningful plasma volumes by using a less invasive blood sampling method than donation of venous blood and that does not require specially trained personnel or specialized equipment.

Notably, similar results were also achieved when similar devices having an extraction member made from another clinically-approved polymer, polyether ether ketone (PEEK) (Panayotov, I. V., Orti, V., Cuisiner, F. & Yachouh, J. Polyetheretherketone (PEEK) for medical applications. *J Mater Sci Mater Med* 27, 118 (2016)) were used.

Example 3: Analytical Suitability of the Human Plasma (Preservation of Analytes) Obtained by the Device According to the Present Invention In the follow-up experiments the suitability of the capillary human plasma (preservation of analytes) obtained to reproducibly measure changes in the concentration of meaningful proteins was tested.

To this end, a volunteer applied its capillary blood to four devices (as explained above). In the following, different preservation conditions were applied to each of the devices:
1. First device: first, the micro-pillar extraction member disc was preloaded with 5 µl of a urea-based denaturing solution (7M Urea prepare in sterile water) that was let at room temperature until all water evaporated. After assembling the whole device (following the arrows in FIG. 1A), the sampling and plasma separation procedure as described in Example 2 was followed and the device was closed with the lid and immediately stored for 48 hours at +4° C. hours.
2. Second device: first, the micro-pillar disc extraction member was preloaded with 5 µl of a urea-based denaturing solution that was let at room temperature until all water evaporated. After assembling the whole device (following the arrows in FIG. 1A), the above-explained sampling procedure (the same as for FIG. 3) was followed and the device was closed with the lid incorporating a desiccant pellet (TBM33®, Wisepac). Finally, the device was stored at room temperature for 48 hours.
3. Third device: first, the micro-pillar extraction member disc was substituted by a 903 Protein Saver paper disc (of 1 cm of diameter). After assembling the whole device (following the arrows in FIG. 1A), the sampling and plasma separation procedure as described in Example 2 was followed and the filter was removed and dried at room temperature for 30 minutes. Next, the paper was introduced in a light-protected bag provided with a desiccant. The bag was closed and immediately stored at +4° C. for 48 hours.
4. Fourth device: first, the micro-pillar extraction member disc was substituted by a 903 Protein Saver paper disc (of 1 cm of diameter). After assembling the whole device (following the arrows in FIG. 1A), the sampling and plasma separation procedure as described in Example 2 was followed and the filter was removed and let dry at room temperature for 30 minutes. Next, the paper was introduced in a light-protected bag provided with a desiccant. The bag was closed and immediately stored at room temperature for 48 hours.

As an additional control of the experiment, all these four capillary plasma samples were compared to a control sample consisting of 10 µl of human plasma obtained by a fingerprick and centrifugation (2500 g for 10 minutes at +4° C.), collected from the same individual before the capillary samples were applied to the four devices. The control sample was stored at −80° C., which is very effective in preserving samples but not user-friendly and applicable to a home service use. After 48 hours, these five plasma samples were analyzed using:
  i) a state-of-the-art targeted proteomic method named Data Independent Acquisition Mass Spectrometry (DIA-MS; see e.g. Rouwette, T., Sondermann, J., Avenali, L., Gomez-Varela, D. & Schmidt, M. Standardized Profiling of The Membrane-Enriched Proteome of Mouse Dorsal Root Ganglia (DRG) Provides Novel Insights Into Chronic Pain. *Molecular & cellular proteomics: MCP* 15, 2152-2168 (2016)), which measures changes in concentration of hundreds of specific proteins with very high reproducibility.
  ii) Targeted metabolomics using the AbsoluteIDQ p180k Biocrates metabolomic kit and service (Biocrates Life Sciences AG, Innsbruck) that measures the absolute concentration of 180 metabolites with high accuracy and sensitivity.

FIG. 3A shows the number of peptides detected in all five samples using DIA-MS. Importantly, the overall number of peptides detected (as a direct measurement of protein preservation) are comparable between the control sample and the two capillary samples obtained using the sampling devices of the present invention at any of the two storage temperatures. In contrast, more than 50% of these peptides were not detected when using the 903 paper based device.

FIG. 3B shows the number of metabolites detected in all five samples using the AbsoluteIDQ p180k Biocrates metabolomic mass spectrometry kit. The number of metabolites detected (as a direct measurement of metabolite preservation) was increased in the plasma samples that were received with a device according to the present invention and stored in the PA extraction member disc of the device according to the present invention compared to the samples received with a 903 paper-based device and stored on the 903 paper. These differences in preservation depend on the type of metabolite studied, being very considerable for Acylcarnitines and significant for Phosphatidylcholines.

Therefore, separating and preserving/storing plasma or serum with the device according to the present invention seems to be particularly advantageous for analytes that are proteins and metabolites (such as in particular Acylcarnitines or Phosphatidylcholines).

The results demonstrate the superior preservation performance of the device of the present invention (based on a micro-pillar extraction member) compared to current state-of-the-art paper-based solutions (e.g. 903 Protein Saver used in drop blood paper) for the detection of clinically meaningful metabolites and proteins in human plasma.

Example 4: Analytical Suitability of the Human Plasma (Number of Proteins Detected) Obtained by the Device According to the Present Invention In the follow-up experiments the suitability of the capillary human plasma obtained to reproducibly measure changes in the concentration of meaningful proteins was tested. To this end, a volunteer applied its capillary blood to three devices (as explained above). In the following, a different preservation condition was applied to each of the devices:
1. First device: first, the micro-pillar extraction member disc was preloaded with 5 µl of a urea-based denaturing solution that was let at room temperature until all water evaporated. After assembling the whole device (following the arrows in FIG. 1A), the sampling and plasma separation procedure as described in Example 2 was followed and the device was closed with the lid and immediately stored in dry ice for 48 hours.
2. Second device: first, the micro-pillar extraction member disc was preloaded with 5 µl of a urea-based denaturing solution that was let at room temperature until all water evaporated. After assembling the whole device (following the arrows in FIG. 1A), the sampling and plasma separation procedure as described in Example 2 was followed and the device was closed with the lid and immediately stored at +4° C. for 48 hours.
3. Third device: first, the micro-pillar disc extraction member was preloaded with 5 µl of a urea-based denaturing solution that was let at room temperature until all water evaporated. After assembling the whole device (following the arrows in FIG. 1), the above-explained sampling procedure (the same as for FIG. 3) was followed and the device was closed with the lid incorporating a desiccant pellet (TBM33®, Wisepac). Finally, the device was stored at room temperature for 48 hours.

As a control of the experiment, all these three capillary plasma samples were compared to a control sample consisting of 10 µl of human plasma obtained by classical venipuncture and centrifugation (2500 g for 15 minutes at room temperature), collected from the same individual by a trained technician immediately before the capillary samples were applied to the three devices and stored at −80° C. After 48 hours, these four plasma samples were analyzed using a state-of-the-art targeted proteomic method named Data Independent Acquisition Mass Spectrometry (DIA-MS; see e.g. Rouwette, T., Sondermann, J., Avenali, L., Gomez-Varela, D. & Schmidt, M. Standardized Profiling of The Membrane-Enriched Proteome of Mouse Dorsal Root Ganglia (DRG) Provides Novel Insights Into Chronic Pain. *Molecular & cellular proteomics: MCP* 15, 2152-2168 (2016)), which measures changes in concentration of hundreds of specific proteins with very high reproducibility.

FIG. 4 shows the measurement of 511 proteins in all four samples using DIA-MS. Importantly, the overall protein intensity values (as a direct measurement of protein amount) are comparable between the control sample and all three capillary samples obtained using the sampling devices (regression coefficients >0.88 for all three comparisons). Importantly, the storage conditions did not show any deleterious influence in the overall protein landscape (even when the sample was stored at room temperature for 2 days).

Further analysis of the results demonstrates the ability to detect and quantify clinically meaningful protein biomarkers. The results show the profiling of 9 FDA approved cancer biomarkers (FIG. 5) as well as 32 proteins proposed as biomarkers for Ovarian cancer (Huttenhain, R. et al. Reproducible quantification of cancer-associated proteins in body fluids using targeted proteomics. *Science translational medicine* 4, 142ra194 (2012)) (FIG. 6), among them four of the five proteins (B2MG, APOA1, TTHY and TRFE) belonging to the commercially available and FDA-approved OVA@ biomarker panel (blood test used to help evaluating the risk of ovarian cancer using antibody-based assays; property of Aspira Labs), at comparable concentrations among the four plasma samples.

Further, the results demonstrate the ability to monitor other clinically meaningful physiological processes such as metabolic processes (FIG. 7), as well as proteins belonging to commercial panels currently offered to costumers but measured using antibodies (such as CRP, ApoA1, Albumin or IGF-1; analyzed by WellnessFX).

Finally, the results also demonstrate the suitability of the samples obtained by the device of the present invention to be used for the discovery of new protein biomarkers, which are thought to belong to the proteins secreted by the different organs into the blood stream and therefore present at low concentration (ng/ml range) in blood. Twenty six proteins in the low ng/ml concentration range could be detected (e.g. IGF1, ADIPOQ, GP1BA or CBPB2; empty squares in FIG. 8 represent proteins with concentrations below 50 ng/ml in human plasma according to Farrah et al., Molecular Cellular Proteomics, 2011), despite that the plasma samples were not depleted from the most abundant proteins (a usual procedure in order to detect low abundant proteins in plasma).

In summary, the results clearly show the successful performance of the presented device to target the detection and discovery of meaningful protein and metabolite biomarkers in blood samples. The easy use of the device, the possibility to store at +4° C. or even at room temperature for at least 2 days, as well as the possibility to manufacture the device using mass production techniques (e.g. injection molding or hot embossing) make this device suitable for point of care (POC) or direct-to-costumer services.

While aspects of the invention are illustrated and described in detail in the figures and in the foregoing description, such illustration and description is to be considered illustrative or exemplary and not restrictive. Also reference signs in the claims should not be construed as limiting the scope.

It will also be understood that changes and modifications may be made by those of ordinary skill within the scope and spirit of the following claims. In particular, the present invention covers further embodiments with any combination of features from different embodiments described above. It is also to be noted in this context that the invention covers all further features shown in the figures individually, although they may not have been described in the previous or following description. Also, single alternatives of the embodiments described in the figures and the description and single alternatives of features thereof can be disclaimed from the subject matter according to aspects of the invention.

Whenever the word "comprising" is used in the claims, it should not be construed to exclude other elements or steps. Similarly, the indefinite article "a" or "an" does not exclude a plurality. A single unit may fulfill the functions of several features recited in the claims. It should also be understood that the terms "essentially", "substantially", "about", "approximately" and the like used in connection with an attribute or a value may define the attribute or the value in an exact manner in the context of the present disclosure. The terms "essentially", "substantially", "about", "approximately" and the like could thus also be omitted when referring to the respective attribute or value.

The invention claimed is:

1. A method for analyzing one or more analytes contained in plasma or serum separated from a blood sample, the method comprising:
   a) separating plasma or serum from a blood sample using a device comprising:
      a housing with a housing base,
      a separation member configured to separate plasma or serum from cellular blood components by retaining said cellular blood components, wherein said separation member has a separation member upper surface and an opposing separation member lower surface, wherein at least a portion of the separation member upper surface is configured to receive the blood sample,
      an extraction member for extracting the separated plasma or serum from the separation member,
      a sample introduction member, said sample introduction member being disposed above the separation member and having a configuration that allows the blood sample to be applied onto the separation member upper surface, and
      a desiccant;
      wherein the device is configured to be provided in a first configuration and in a second configuration;
      wherein, in the first configuration, the separation member lower surface is in contact with an extraction member upper surface; and
      wherein, in the second configuration, the separation member is moved away from the extraction member;
   b) introducing the blood sample;
   c) separating the plasma or serum by waiting for a predetermined period of time;
   d) desiccating the separated plasma or serum in the extraction member by the desiccant;
   e) dissolving a desiccation product resulting from step d) in an aqueous solution; and
   f) analyzing said one or more analytes in the separated plasma or serum.

2. The method of claim 1, wherein analyzing the one or more analytes in step f) comprises analyzing the one or more analytes by a proteomic based method including mass spectrometry.

3. The method of claim 1, wherein the sample introduction member comprises a recess in which the desiccant is received.

4. The method of claim 3, wherein the extraction member is received in one or more protrusions and/or one or more recesses of the housing base, wherein said one or more protrusions and/or one or more recesses of the housing base seal with a rim of the recess in which the desiccant is received when the device is in the second configuration.

5. The method according to claim 1, wherein the device is configured to be shifted from the first configuration to the second configuration by moving the sample introduction member and the housing base with respect to each other.

6. The method according to claim 1, wherein the device is configured to be shifted from the first configuration to the second configuration by rotating the sample introduction member and the housing base against each other for a predefined angle.

7. The method according to claim 6, wherein the sample introduction member is connected to the housing base such that the sample introduction member and the housing base are rotatable against each other about a longitudinal axis of the device.

8. The method of claim 7, wherein the sample introduction member is connected to the housing base by a threading or a bayonet connection.

9. The method of claim 1, wherein the desiccant is positioned directly above the extraction member when the device is in the second configuration.

10. The method of claim 1, wherein the device further comprises a protection membrane interposed between the desiccant and the extraction member, wherein the protection membrane allows air exchange.

11. The method of claim 1, wherein the sample introduction member is bonded to the separation member upper surface.

12. The method of claim 11, wherein the sample introduction member is bonded to the separation member upper surface by an adhesive, heat and/or ultrasonic welding.

13. The method of claim 1, wherein the sample introduction member is provided with one or more through holes through which the blood sample is applied.

14. The method of claim 13, wherein the device further comprises a housing lid, wherein the housing lid is provided with at least one projection that protrudes into at least one of the through holes.

15. The method of claim 1, wherein in step b) capillary blood is applied drop-wise to the device as the blood sample.

16. The method of claim 1, wherein the desiccant is a desiccant pellet.

17. A device for separation of plasma or serum from a blood sample, wherein said device comprises:
   a housing with a housing base,
   a separation member configured to separate plasma or serum from cellular blood components by retaining said cellular components of blood, wherein said separation member has a separation member upper surface and an opposing separation member lower surface, wherein at least a portion of the separation member upper surface is configured to receive the blood sample, and
   an extraction member for extracting the separated plasma or serum from the separation member,
   a sample introduction member, said sample introduction member being disposed above the separation member and having a configuration that allows the blood sample to be applied onto the separation member upper surface, and
   a desiccant;
   wherein the sample introduction member comprises a recess in which the desiccant is received;
   wherein the desiccant is configured to desiccate the separated plasma or serum in the extraction member;

wherein the device is configured to be provided in a first configuration and in a second configuration;

wherein, in the first configuration, the separation member lower surface is in contact with an extraction member upper surface;

wherein, in the second configuration, the separation member is moved away from the extraction member; and wherein one or more protrusions and/or one or more recesses of the housing base seal with a rim of the recess in which the desiccant is received when the device is in the second configuration.

18. The device of claim 17, wherein said extraction member is disposed below said separation member.

19. The device of claim 17, wherein the device is configured to be shifted from the first configuration to the second configuration by rotating the sample introduction member and the housing base against each other for a predefined angle.

20. The device of claim 17, wherein the sample introduction member is bonded to the separation member upper surface by an adhesive, heat and/or ultrasonic welding.

* * * * *